United States Patent [19]

Suzuki et al.

[11] Patent Number: 5,371,225

[45] Date of Patent: Dec. 6, 1994

[54] TETRACYCLIC COMPOUNDS

[75] Inventors: Fumio Suzuki, Mishima; Yoshisuke Nakasato; Hiroshi Tsumuki, both of Sunto; Kenji Ohmori, Mishima; Hiroshi Nakajima, Sunto; Tadafumi Tamura, Numazu; Soichiro Sato, Sunto, all of Japan

[73] Assignee: Kyowa Hakko Kogyo Co., Ltd., Tokyo, Japan

[21] Appl. No.: 170,192

[22] PCT Filed: Apr. 23, 1993

[86] PCT No.: PCT/JP93/00527

§ 371 Date: Dec. 22, 1993

§ 102(e) Date: Dec. 22, 1993

[87] PCT Pub. No.: WO93/22286

PCT Pub. Date: Nov. 11, 1993

[30] Foreign Application Priority Data

Apr. 24, 1992 [JP] Japan .................. 4-106482
Dec. 22, 1992 [JP] Japan .................. 4-342710

[51] Int. Cl.$^5$ .................. A61K 31/44; C07D 221/18
[52] U.S. Cl. .................. 546/61
[58] Field of Search .................. 546/61; 514/284

[56] References Cited

U.S. PATENT DOCUMENTS 4,918,077 4/1990 Behrens .................. 514/284
5,084,462 1/1992 Ackerman et al. .................. 514/311

FOREIGN PATENT DOCUMENTS

WO00739 1/1992 WIPO .

OTHER PUBLICATIONS

Huisgen et al., Liebigs Ann. Chem., vol. 610 (1957) 57–66.

*Primary Examiner*—Johann Richter
*Assistant Examiner*—Catherine S. Kilby Scalzo
*Attorney, Agent, or Firm*—Fitzpatrick, Cella, Harper & Scinto

[57] ABSTRACT

The present invention relates to novel tetracyclic compounds represented by formula (I)

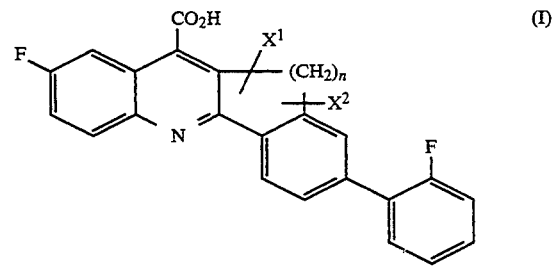

(wherein each of $X^1$ and $X^2$ independently represents hydrogen or lower alkyl; n represents an integer of 1 to 4), or a pharmaceutically acceptable salt thereof, which are useful as immunosuppressive agents.

1 Claim, 1 Drawing Sheet

TETRACYCLIC COMPOUNDS

This application is a 371 of PCT/JP93/00527 filed Apr. 23, 1993.

TECHNICAL FIELD

The present invention relates to novel tetracyclic compounds which are useful as immunosuppresive agents.

PRIOR ART

A compound represented by the formula

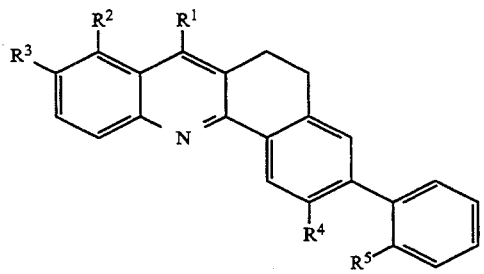

(where $R^1$ represents $CO_2H$, etc.; $R^2$ and $R^3$ independently represent H, F, etc.; and $R^4$ and $R^5$ independently represent H, etc.) is disclosed in Japanese Published Unexamined Patent Application No. 233661/90 corresponding to U.S. Pat. No. 4,918,077 as being effective as a cancer chemotherapeutic agent, and in WO 92/00739, it is mentioned as being useful as an immunosuppresive agent.

The compound sodium 2- (2 '-fluoro-1, 1'-biphenyl-4-yl) -6-fluoro-3-methyl-4-quinoline carboxyl disclosed in Japanese Published Unexamined Patent Application No. 313428/89 corresponding to U.S. Pat. No. 5,084,462 as being useful as an immunosuppresive agent.

The compounds 5H-indeno [1,2-b]quinoline-6-carboxylic acid; 6, 7-dihydro-5H-benzo[6, 7]cyclohepta [1,2-b]quinoline-8-carboxylic acid and 5, 6, 7,8-tetrahydrobenzo [7,8]cycloocta[1,2-b]quinoline-9-carboxylic acid have been reported, but their pharmacological effects are unknown [(Liebigs Ann. Chem., 610, 57 (1957) ].

DISCLOSURE OF THE INVENTION

According to the present invention, there are provided novel tetracyclic compounds represented by formula (I)

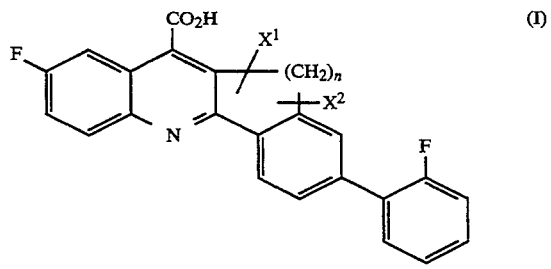

(wherein $X^1$ and $X^2$ independently represent hydrogen or lower alkyl; and n represents an integer of 1 t6 4) and pharmaceutically acceptable salts thereof.

In the definition of the respective groups in formula (I), the lower alkyl includes straight-chain or branched alkyl group having 1 to 6 carbon atoms, for example, methyl, ethyl, propyl, isopropyl, butyl, isobutyl, sec-butyl, tertbutyl, pentyl, neopentyl, hexyl, etc.

The pharmaceutically acceptable salts of Compound (I) include metal salts, ammonium salts, organic amine addition salts and amino acid addition salts.

As the pharmaceutically acceptable metal salts of Compound (I) include alkali metal salts such as sodium salt and potassium salt, alkaline earth metal salts such as magnesium salt and calcium salt, aluminum salts and zinc salt; as the pharmaceutically acceptable ammonium salts include salts of ammonium and tetramethylammonium; as the pharmaceutically acceptable organic amine addition salts include addition salts with morpholine and piperidine; and as the pharmaceutically acceptable amino acid addition salt include addition salts with lysine, glycine and phenylalanine. The processes for producing the compounds of the present invention are described below.

PROCESS 1

Compound (I-a), Compound (I) wherein $X^1$ and $X^2$ are both hydrogen, can be obtained by the following reaction steps.

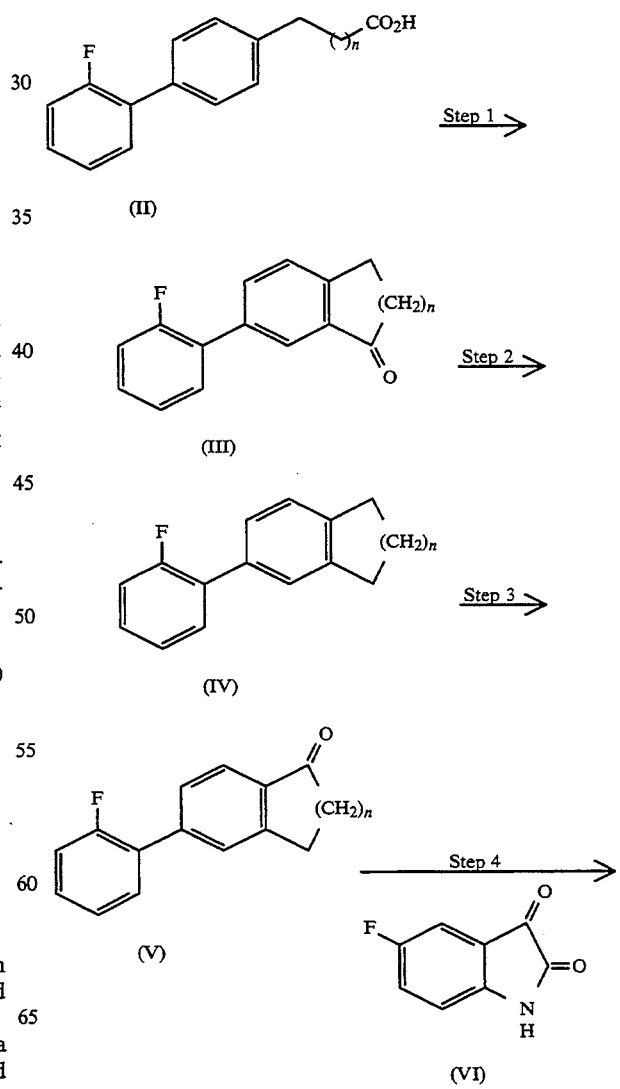

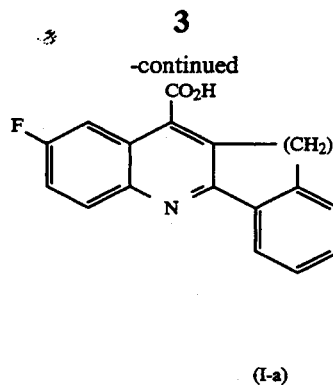

(I-a)

(In the above formulae, n has the same meaning as defined above.)

STEP 1

Compound (III) can be obtained by treating Compound (II) with a dehydrating agent in the absence of a solvent usually at 50° to 120° C. for 1 to 6 hours.

The dehydrating agent includes polyphosphoric acid, methanesulfonic acid and sulfuric acid.

STEP 2

Compound (IV) can be obtained by reacting Compound (III) with 2 to 3 equivalents of triethylsilane in trifluoroacetic acid usually at room temperature to 70° C. for 5 minutes to 6 hours.

STEP 3

Compound (V) can be obtained by reacting Compound (IV) with 1 to 4 equivalents of chromic acid in a mixed solvent of acetic acid/propionic acid usually at 0° C. to room temperature for 1 to 6 hours.

STEP 4

Compound (I-a) can be obtained by reacting Compound (V) with an equivalent amount of Compound (VI) (product of Aldrich Co.) in a mixed solvent of ethanol/water under the alkaline condition where potassium hydroxide, sodium hydroxide, etc. are used usually at room temperature to 100° C. for 12 to 120 hours. Compound (II) can be obtained by the following reaction steps.

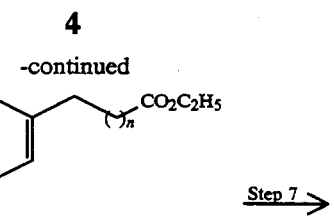

(X)

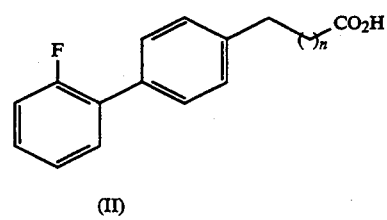

(II)

(In the above formulae, n has the same meaning as defined above.)

STEP 5

Compound (IX) can be obtained by reacting Compound (VII) (product of Aldrich Co.) with an equivalent amount of Compound (VIII) in an inert solvent such as dichloromethane and dichloroethane in the presence of 2 equivalents of a Lewis acid such as aluminum trichloride usually at 0° C. to room temperature for 1 to 12 hours.

STEP 6

Compound (X) can be obtained #rom Compound (IX) by the same method as in Step 2 above.

STEP 7

Compound (II) can be obtained by reacting Compound (X) in a mixed solvent of dioxane/water under the alkaline condition where potassium hydroxide, sodifim hydroxide, etc. are used usually at room temperature to 100° C. for 1 to 12 hours.

As an alternative method, Compound (II-a), wherein n in the starting Compound (II) is 2 or 3, can be obtained by the following reaction steps.

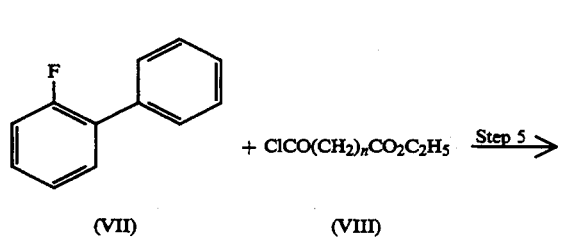

(VII)      (VIII)

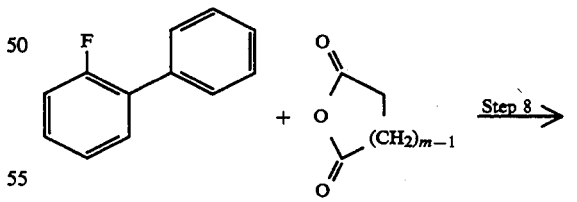

(VII)      (XI)

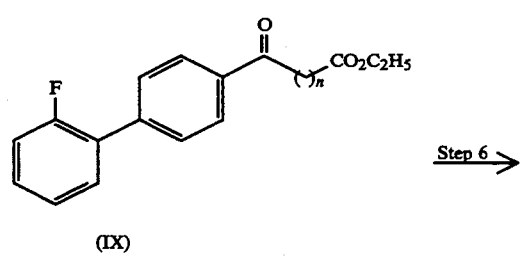

(IX)

(XII)

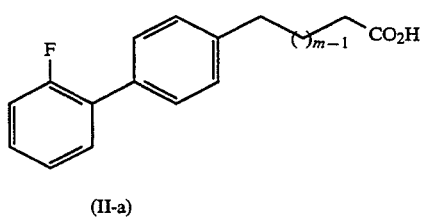

(II-a)

(In the above formulae, m represents 2 or 3.)

STEP 8

Compound (XII) can be obtained from Compound (VII) (product of Aldrich Co.) and an equivalent amount of Compound (XI) (product of Aldrich Co.) by approximately the same method as in Step 5 above.

STEP 9

Compound (II-a) can be obtained from Compound (II) by approximately the same method as in Step 2 above.

Compound (V) can be obtained by the following reaction step.

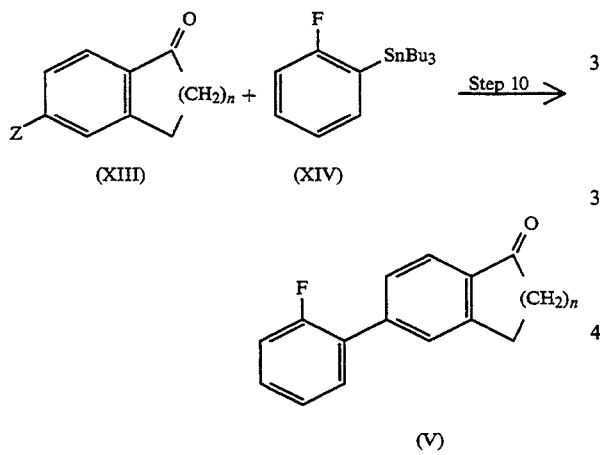

(In the above formulae, n has the same meaning as defined above, Bu represents butyl, and Z represents bromine, iodine or trifluorosulfonyloxy.)

STEP 10

Compound (V) can be obtained by reacting Compound (XIII) with 1 to 2 equivalents of Compound (XIV) in a solvent such as dimethylformamide, tetrahydrofuran and dioxane in the presence of a catalytic amount of a palladium complex usually at 60° to 120° C. for 1 to 12 hours. If necessary, a salt such as lithium chloride or an oxidizing agent such as silver oxide may be added thereto.

Compound (XIII) may be synthesized by the known method J. Org. Chem. 27, 70 (1962)]or a similar method. Also, compound (XIV) may be synthesized by the known method Angew. Chem., Int. Ed. Engl., 25, 508 (1986)]or a similar method.

A compound wherein $X^1$ and/or $X^2$ in Compound (I) are lower alkyl may be obtained by the following Processes 2 to 4.

PROCESS 2

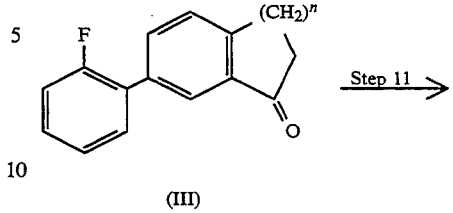

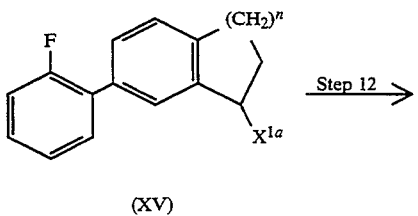

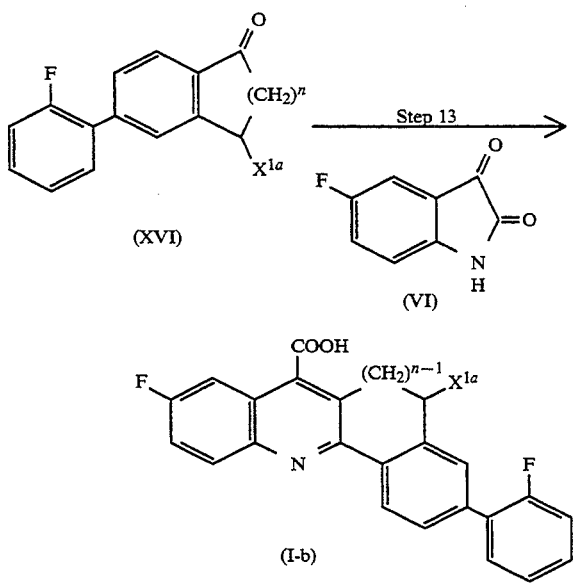

(In the above formulae, n has the same meaning as defined above, and $X^{1a}$ represents the lower alkyl in the definition of $X^1$.)

STEP 11

Compound (XV) can be obtained by reacting Compound (III) with an equivalent amount of an alkylphosphonium salt in a solvent such as tetrahydrofuran, dioxane, dimethylformamide and dimethylsulfoxide in the presence of a base usually at 0° to 120° C. for 5 minutes to 12 hours, and then carrying out catalytic hydrogenation with a catalyst such as palladium/carbon and platinum dioxide, in a solvent such as methanol, ethanol and acetic acid usually at 0 to 100° C. for 5 minutes to 12 hours.

As the base, n-butyl lithium, potassium tert-butoxide, sodium hydride, sodium hydroxide, potassium carbonate, triethylamine are exemplified.

As an alternative method of Step 11, Compound (XV) can be obtained by reacting Compound (III) with 1 to 5 equivalents of a Grignard reagent in a solvent such as ether, tetrahydrofuran and dioxane at −30° to 100° C. for 5 minutes to 12 hours, and then reacting the product with 1 to 2 equivalents of triethylsilane in trifluoroacetic acid usually at room temperature to 70° C. for 5 minutes to 6 hours.

STEP 12

Compound (XVI) can be obtained from Compound (XV) by the same method as in Step 3 above.

STEP 13

Compound (I-b) can be obtained from Compound (XVI) and Compound (VI) by the same method as in Step 4 above.

PROCESS 3

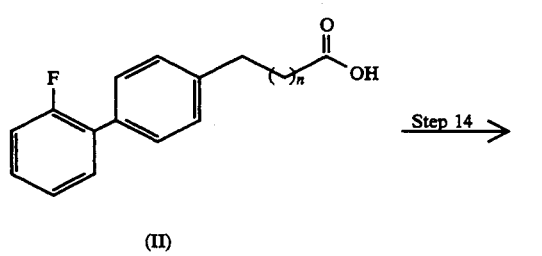

(II)

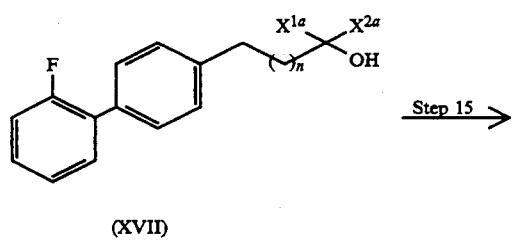

(XVII)

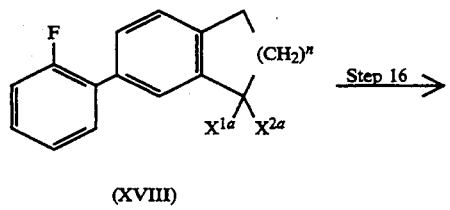

(XVIII)

(XIX)

(VI)

(I-c)

(In the above formulae, $X^{1a}$ and n have the same meanings as defined above and $X^{2a}$ represents the lower alkyl in the definition of $X^2$.)

STEP 14

Compound (I) can be obtained by reacting Compound (II) with 2 to 10 equivalents of a Grignard reagent in a solvent such as ether, tetrahydrofuran and dioxane usually at −30° to 100° C. for 5 minutes to 12 hours.

STEP 15

Compound (XVIII) can be obtained by treating Compound (XVII) in an inert solvent such as dichloromethane and dichloroethane in the presence of an equivalent amount of a Lewis acid such as aluminum trichloride usually at 0° C. to room temperature for 1 to 12 hours.

STEP 16

Compound (XIX) can be obtained from Compound (XVIII) by the same method as in Step 3 above.

STEP 17

Compound (I-c) can be obtained from Compound (XIX) and Compound (VI) by the same method as in Step 4 above.

PROCESS 4

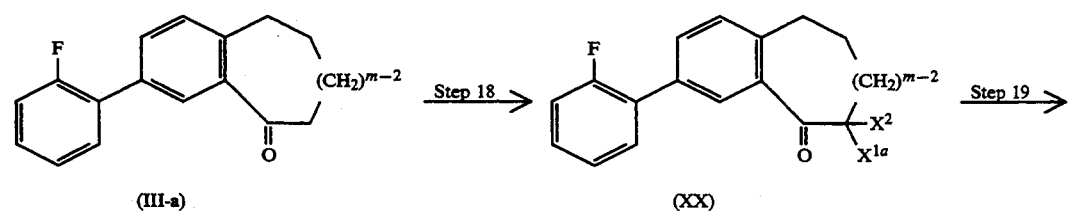

(III-a)    (XX)

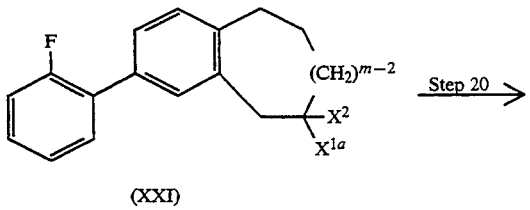

(XXI)

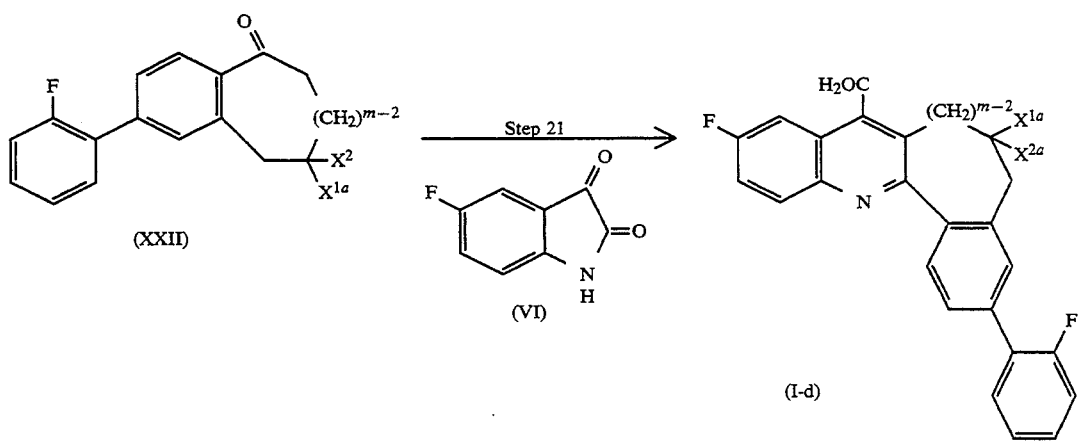

(In the above formulae $X^{1a}$ $X^2$ and m have the same meanings as defined above.)

STEP 18

Compound (XX) may be obtained by reacting Compound (III-a), Compound (III) wherein n is 2 or 3, with an alkyl halide such as methyl iodide and ethyl iodide in a solvent such as tetrahydrofuran, dioxane, dimethylformamide and dimethylsulfoxide in the presence of a base usually at 0 to 120° C. for 5 minutes to 12 hours.

As the base, sodium hydride, potassium tert-butoxide, sodium hydroxide, potassium carbonate are exemplified. If necessary, a quaternary ammonium halide such as tetrabutylammonium bromide or a phase-transfer catalyst such as 18-crown-6 or another crown ether may be added thereto.

As an alternative method of Step 18, Compound (XX) can be obtained by reacting Compound (III-a) with a secondary amine such as pyrrolidine and piperazine in a solvent such as benzene and toluene in the presence of p-toluenesutfonic acid usually under reflux for 1 to 12 hours, and then reacting the product with an alkyl halide such as methyl iodide and ethyl iodide in a solvent such as dioxane and dimethylformamide usually at room temperature to 100° C. for 5 minutes to 12 hours.

STEP 19

Compound (XXI) can be obtained from Compound (XX) by the same method as in Step 2 above.

STEP 20

Compound (XXII) can be obtained from Compound (XXI) by the same method as in Step 3 above.

STEP 21

Compound (I-d) can be obtained from Compound (XXII) and Compound (VI) by the same method as in Step 4 above.

The intermediates and the desired compounds in the processes described above may be isolated and purified by purification methods conventionally used in organic synthetic chemistry, for example, filtration, extraction, washing, drying, concentration, recrystallization, and various kinds of chromatography. The intermediates may also be subjected to the subsequent reaction without purification.

In the case where a salt of Compound (I) is desired and it is produced in the form of the desired salt, it may be subjected to pruification as such. In the case where Compound (I) is produced in the free form and its salt is desired, it may be dissolved or suspended in an appropriate solvent, and then an acid or a base may be added thereto to the solution or suspension to form its salt.

Compound (I) and pharmaceuticaly acceptable salt thereof may be in the form of adducts with water or various solvents, which are also included in the scope of the present invention.

Specific examples of Compound (I) obtained by the respective processes are shown in Table 1.

TABLE 1

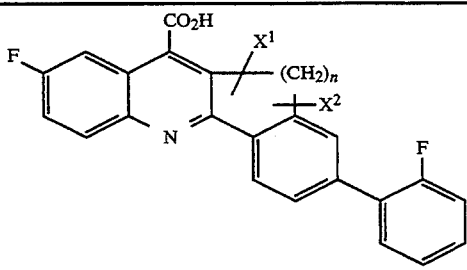

| Compound No. | n | $X^1$ | $X^2$ |
|---|---|---|---|
| 1 | 1 | H | H |
| 2 | 2 | H | H |
| 3 | 3 | H | H |
| 4 | 4 | H | H |
| 5 | 2 | 5-$CH_3$ | H |
| 6 | 2 | 5-$C_2H_5$ | H |
| 7 | 2 | 5-$CH_3$ | 5-$CH_3$ |
| 8 | 2 | 6-$CH_3$ | H |
| 9 | 3 | 5-$CH_3$ | H |

TABLE 1-continued

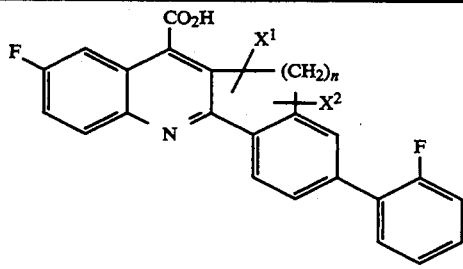

| Compound No. | n | $X^1$ | $X^2$ |
|---|---|---|---|
| 10 | 3 | 6-$CH_3$ | H |
| 11 | 3 | 6-$CH_3$ | 6-$CH_3$ |

The pharmacological activities of Compound (I) are illustrated with the following test examples.

TEST EXAMPLE 1

Plaque Forming Cell Assay

The plaque forming cell assay was carried out by the following manner with reference to the method of Jerne et al. [Science, 140, 405 (1963)] and the method of Yamamoto et al. [Drugs Experimental Clinical Research, III(1), 5 (1982)].

Male Balb/c strain mice (7-week-old) (Charles River Co.) were sensitized with $1 \times 10^8$ sheep erythrocytes (product of Biotest Research Institute) administered via the caudal vein, and the spleens were extirpated after 6 or 7 days after the sensitization. The extirpated spleens were immersed in Hanks' solution (Nissui Seiyaku) to make a cell suspension, which was then filtered, followed by centrifugal separation at 1200 rpm for 5 minutes. After centrifugal separation, the supernatant was discarded and the precipitate was treated with Tris·$NH_4Cl$ solution to remove the erythrocytes, and then washed three times with Hanks' solution. After discarding the supernatant, the cells were suspended in an RPMI-1640 medium (Nissui Seiyaku) containing 10% bovine fetal serum (Gibco Co.), 50 μg/ml of streptomycin (Meiji Seika), 50 μU/ml of penicillin (Meiji Seika) and 2mercaptoethanol ($5 \times 10^{-5}$M). In each well of a micro culture plate (NUNK Co., Ltd., 24 wells) were put 2 ml of the mixture of the cell suspension containing $1 \times 10^7$ of spleen cells, $5 \times 10^6$ sheep erythrocytes and a test compound solution ($10^{-6}$ M) obtained by diluting the test compound dissolved in dimethylsulfoxide ($10^{-2}$ M) with the above mentioned RPMI-1640, and the cells were cultured at 37° C. for 5 days.

After the completion of the culturing, the cells were subjected to centrifugal separation at 2000 rpm for 5 minutes, and the resulting supernatant was removed. The precipitate was suspended in 1 ml of Hanks' solution, again subjected to centrifugal separation, suspended in 1 ml of Hanks' solution, and then, 50 μl of the suspension and 50 μl of sheep erythrocytes were added to 400 μl of 0.25% agarose/Hanks' solution heated to 50° C. in advance, and the mixture was scattered on a glass slide, placed on a plaque assay plate, and together with guinea pig complement (Cedarlene Institute) diluted 40-fold with a phosphate buffer solution, incubated at 37° C. for 1 to 2 hours. The number of the appearing direct plaque cells (direct PFC count) in suspension was counted.

The inhibition rate of the antibody production of the test compound was determined by the following equation.

$$\text{inhibition rate (\%)} = \frac{\text{PFC count in control} - \text{PFC count in the presence of test compound}}{\text{PFC count in control}} \times 100$$

The compound used for comparison was 5,6-dihydro-9-fluoro-3-phenylbenz[c]acridine-7-carboxylic acid [Japanese Published Unexamined Patent Application No. 233661/90, hereinafter referred to as Compound (A)] represented by formula (A).

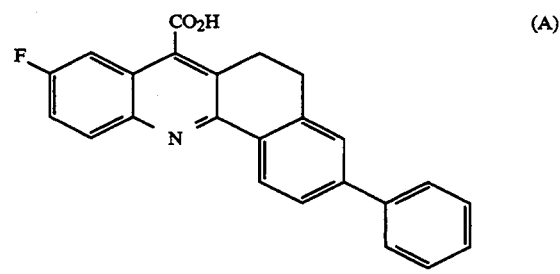

(A)

PFC count in control means PFC count in the absence of the test compound (dimethylsulfoxide alone).
The results are shown in Table 2.

TABLE 2

| Compound No. | Concentration (M) | Inhibition rate (%) |
|---|---|---|
| 2 | $10^{-5}$ | 99.4 |
|   | $10^{-6}$ | 94.4 |
|   | $10^{-7}$ | 57.1 |
| 3 | $10^{-5}$ | 83.5 |
|   | $10^{-6}$ | 80.3 |
|   | $10^{-7}$ | 55.4 |
| 5 | $10^{-5}$ | 98.7 |
|   | $10^{-6}$ | 64.6 |
| 7 | $10^{-5}$ | 98.1 |
|   | $10^{-6}$ | 75.3 |
| 8 | $10^{-5}$ | 98.7 |
|   | $10^{-6}$ | 80.2 |
| A | $10^{-5}$ | 78.6 |
|   | $10^{-6}$ | 45.9 |

TEST EXAMPLE 2

Prophylactic Effect Against Adjuvant Arthritis

The experiment was carried out by using groups 7-weeks-old female Lewis rats (Charles River Co.), each group consisting of 8 rats. Following the method of Newbould B.B. [Brit. J. Pharmacol., 21, 127 (1963)], Mycobacterium butylicum (killed and dried) (Difco Co.) suspended in liquid paraffin (0.6 mg/0.1 ml) was subcutaneously injected, as an adjuvant, into right hind paw of rats, hind paws volumes of which were measured in advance. After the injection, the hind paws volumes were measured using a plethysmograph (Unicom Co., Ltd., TK-101), and the swelling rates were determined by comparing each of the right and left hind paws volumes before the injection with that after the injection.

The test compound (Compound 3) was suspended in a 5% arabic gum solution and orally administered once a day on days 0 to 4, days 7 to 11 and days 14 to 16 provided the day of injection of the adjuvant was counted as day 0.

To the control group was orally administered only a 5% arabic gum solution.

The compound used for comparison was sodium 2-(2'-fluoro-1,1'-biphenyl-4-yl)-6-fluoro-3-methyl-4[Japanese Published Unexamined Patent Application No. 313428/89, hereinafter referred to as Compound (B)]represented by formula (B).

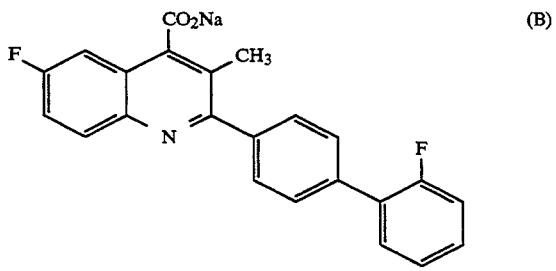

The results are shown in FIGS. 1 and 2.

Depending on the pharmaceutical effects, Compound (I) and its pharmaceutically acceptable salt can be used as they are or in various preparation forms for the desired purpose of administration. The pharmaceutical composition of the present invention can be prepared by uniformly mixing an effective amount of Compound (I) or its pharmaceutically acceptable salt as an active ingredient with a pharmaceutically acceptable carrier. The carrier may be in any of a wide variety of forms, depending on the most preferable form of preparation for administration. The pharmaceutical compositions are preferably in a unit dosage form suitable for oral administration or injection.

In the preparation of pharmaceutical compositions for oral administration, any useful, pharmaceutically acceptable carrier can be used. For example, a liquid preparation for oral administration such as suspension and a syrup can be prepared using water; a sugar such as sucrose, sorbitol and fructose; a glycol such as polyethylene glycol and propylene glycol; an oil such as sesame oil, olive oil and soybean oil; an antiseptic such as alkyl p-hydroxybenzoate; and a flavor such as strawberry flavor and peppermint flavor. Powders, pills, capsules and tablets may be prepared using an excipient such as lactose, glucose, sucrose and mannitol; a disintegrator such as starch and sodium alginate; a lubricant such as magnesium stearate and talc; a binder such as polyvinyl alcohol, hydroxypropyl cellulose and gelatin; a surfactant such as fatty acid esters; and a plasticizer such as glycerin. Tablets and capsules are the most useful oral unit dose forms, since their administration is easy. In the preparation of tablets or capsules, a solid pharmaceutical carrier is used.

A solution for injection may be prepared using a carrier such as distilled water, a saline solution, a glucose solution and a mixture of a saline solution and a glucose solution.

Compound (I) or its pharmaceutically acceptable salts may be administered either orally or parenterally by injection. The effective dose and the administration schedule of Compound (I) or its pharmaceutically acceptable salts vary depending on the mode of administration, age, weight and conditions of a patient, etc. However, it is generally preferred to administer Compound (I) or its pharmaceutically acceptable salts in a dose of 1 to 50 mg/kg per day in 3 to 4 parts.

In the figure, —○—represents the swelling rates of the control group, —△—represents the swelling rates of a comparison compound-administered group (dose: 3 mg/kg) —□—represents the swelling rates of a comparison compound swelling rates a test compound-administered group (dose: administered group (dose: 10 mg/kg), —▲—represents the 1 mg/kg), and —■—represents the swelling rates of a test compound-administered group (dose: 3 mg/kg).

Figure 1:
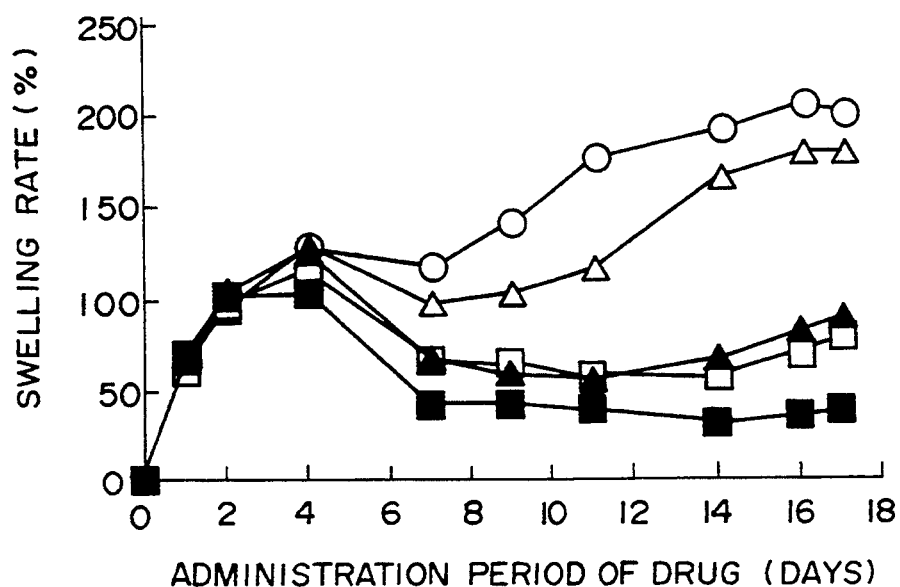
FIG. 1 shows the swelling rates of the rats with right hind paw treated with an adjuvant.
Figure 2:
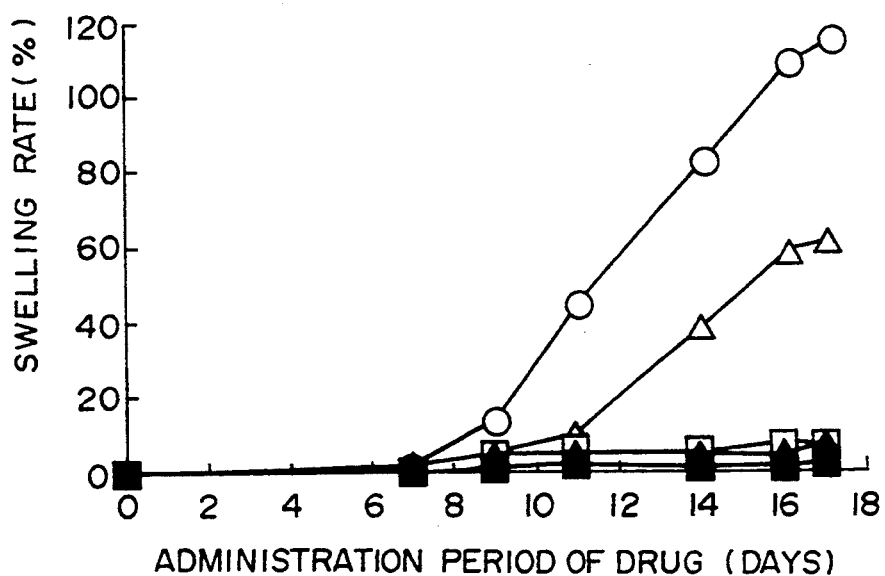

FIG. 2 shows the swelling rates of the rats with the left hind paw untreated with an adjuvant.

In the figure, —○—represents the swelling rates of the control group, —△—represents the swelling rates of a comparison compound-administered group (dose: 3 mg/kg), —□—represents the swelling rates of a comparison compound-administered group (dose: 10 mg/kg), —▲—represents the swelling rates of a test compound-administered group (dose: 1 mg/kg), and —■—represents the swelling rates of a test compound-administered group (dose: 3 mg/kg).

Certain embodiments of the present invention are illustrated in the following Examples, Reference Examples and Preparation Examples.

BEST MODE FOR CARRYING OUT THE INVENTION

Example 1

8-Fluoro-3- ( 2-fluorophenyl ) -5H- indeno [1,2 -b ]quinoline- 6carboxylic acid (Compound 1 )

In 1 ml of water containing 650 mg (10 tool) of potassium hydroxide was dissolved 330 mg (2 tool) of 5fluoroisatin, and 450 mg (2 retool) of Compound c obtained in Reference Example 3 and dissolved in 5 ml of dioxane-ethanol (2:3) was added thereto. After heating to reflux for 3 hours, the solvent was distilled off and ether was added thereto, followed by extraction with water. Hydrochloric acid was added to the aqueous layer, and the precipitated crystals were filtered off. The obtained crystals were washed with water, dried and recrystallized from dimethylformamide-water to obtain 313 mg (42% yield) of the desired compound.

Melting point: >300° C.
Elemental analysis (%): $C_{23}H_{13}F_2NO_2 \cdot 0.5H_2O$;
Calcd.: C 72.25, H 3.69, N 3.66 ;
Found : C 72.35, H 3.39, N 4.07.
IR (KBr) $cm^{-1}$: 1705, 1620, 1505, 1240. NMR (DMSO-$d_6$), δ(ppm): 8.35–8.21(m, 3H),
7.91(s, 1H), 7.78–7.61(m, 3H), 7.53–7.33(m, 3H),
4.40(s, 2H).
MS (m/e): 373 (M+) , 328 [(M-COOH)+]

EXAMPLE 2

5, 6-Dihydro- 9-fluoro-3- ( 2- fluorophenyl ) ben z [c ]acridine-7carboxylic acid (Compound 2)

In 24 ml of ethanol were dissolved 2.66 g (16 mmol) of Compound h obtained in Reference Example 8 and 3.81 g (16 mmol) of 5-fluoroisatin, and 12 ml of water containing 4.22 g (80 mmol) of potassium hydroxide was added thereto. After heating to reflux for 60 hours, the solvent was distilled off, and ether was added thereto, followed by extraction with water. Hydrochloric acid was added to the aqueous layer, the precipitated crystals were filtered off and then washed with ether. The obtained crystals were recrystallized from dimethylformamide-water to obtain 2.6 g (43% yield) of the desired compound.

Melting point: >300° C.
Elemental analysis ( % ): C24H15F2NO2 - 0.2H20;
Calcd.: C 73 . 73, H 3 . 97, N 3 . 58 ;
Found : C 73.65, H 3.73, N 3 . 67.
IR (KBr) cm$^{-1}$: 3400, 1718, 1615, 1502, 1420.
NMR (DMSO-d$_6$), δ(ppm): 8.52(1H, d, J=SHz), 8.23–8.17 ( 1H, m), 7.95–7.32 (8H, m), 3.21–3.07 ( 4H, m).
MS (m/e): 387 (M+).

EXAMPLE 3

6, 7-Dihydro-10-fluoro-3- (2-fluorophenyl) -5Hbenzo [6, 7]cyclohepta [1,2-b]quinoline-8-carboxylic acid ( Compound 3 )

In 4 ml of ethanol were dissolved 0.62 g (2.4 mmol) of Compound m obtained in Reference Example 13 and 0.41 g (2.4 mmol) of 5-fluoroisatin, and 2 ml of water containing 0.67 g (12 mmol) of potassium hydroxide was added thereto. After heating to reflux for 50 hours, the solvent was distilled off, and ether was added thereto, followed by extraction with water. Hydrochloric acid was added to the aqueous layer, the precipitated crystals were filtered off and then washed with ether. The obtained crystals were recrystallized from dimethylformamide-water to obtain 445 mg (46% yield) of the desired compound.

Melting point: >300° C .
Elemental analysis (%): C$_{25}$H$_{17}$F$_2$NO$_2$·O.4H$_2$O;
Calcd.: C 73.49, H 4.39, N 3.43 ;
Found: C 73.55, H 4.04, N 3.34.
IR (KBr) cm$^{-1}$: 2940, 2860, 1730, 1625, 1500, 1480, 1240.
NMR (DMSO-d$_6$), δ(ppm): 8.24–8.19(1H, m), 7.87 (1H, d, J=8Hz), 7.79–7.32 (8H, m), 2.89–2.61(4H, m), 2.26–2.21(2H, m).
MS (m/e): 401 (M+), 356.

EXAMPLE 4

11-Fluoro-3-(2-fluorophenyl)-5,6,7,8tetrahydrobenzo[7,8]cycloocta[1,2-b]quinoline-9-carboxylic acid (Compound 4)

In 7 ml of ethanol were dissolved 0.67 g (2.5 mmol) of Compound n obtained in Reference Example 14 and 0.41 g (2.5 mmol) of 5-fluoroisatin, and 7 ml of 6 N potassium hydroxide was added thereto. After heating to reflux for 24 hours, the solvent was distilled off, and ether was added thereto, followed by extraction with water. Hydrochloric acid was added to the aqueous layer, and the precipitated crystals were filtered off. The obtained residue was separated and purified by silica gel column" chromatography [elution solvent: chloroform-methanol-acetic acid (100:1:0.1)], and then recrystallized from ethanol to obtain 0.60 g (58% yield) of the desired compound.

Melting point: >300° C.
Elemental analysis (%): C$_{26}$H$_{19}$F$_2$NO$_2$·0.5H$_2$O;
Calcd.: C 73.58, H 4.75, N 3.30 ;
Found: C 73.27, H 4.54, N 3.38.
IR (KBr) cm$^{-1}$: 2928, 1702, 1625, 1501, 1486.
NMR (DMSO-d$_6$), δ(ppm): 8.23–8.17(1H, m), 7.79–7.32(9H, m), 3.08–2.85(2H, m), 2.34–1.65 (6H, m).
MS (m/e): 415 (M+).

EXAMPLE 5

5,6-Dihydro-9-fluoro-3-(2-fluorophenyl)-5methylbenz[-c]acridine-7-carboxylic acid (Compound 5)

In 15 ml of ethanol were dissolved 1.26 g (5.0 mmol) of Compound p obtained in Reference Example 16 and 0.82 g (5.0 mmol) of 5-fluoroisatin, and 4 ml of water containing 1.39 g (25 mmol) of potassium hydroxide was added thereto. After heating to reflux for 45 hours, the solvent was distilled off, and ether was added thereto, followed by extraction with water. Hydrochloric acid was added to the aqueous layer, the precipitated crystals were filtered off and then washed with ether. The obtained crystals were recrystallized from ethanol to obtain 0.85 g (43% yield) of the desired compound.

Melting point: 274.1°–277.4° C.
Elemental analysis (%): C$_{25}$H$_{17}$F$_2$NO$_2$·0.4H$_2$O;
Calcd.: C 73.49, H 4.39, N 3.43 ;
Found: C 73.34, H 4.11, N 3.72.
IR (KBr)cm$^{-1}$: 2364, 1626, 1502, 1408, 1366, 1247.
NMR (DMSO-d6), δ(ppm): 8.54(1H, d, J=8Hz), 8.23–8.17(1H, m), 7.76–7.32(8H, m), 3.49–3.23(2H, m), 3.06–2.97(1H, m), 1.22(3H, d, J=7Hz). MS (m/e): 401 (M+) , 386.

EXAMPLE 6

10 5, 6-Dihydro-5-ethyl-9-fluoro-3-(2fluorophenyl)benz [c]acridine-7-carboxylic acid (Compound 6)

In 4 ml of ethanol were dissolved 0.62 g (2.4 mmol) of Compound r obtained in Reference Example 18 and 0.41 g (2.4 mmol) of 5-fluoroisatin, and 2 ml of water containing 0.67 g (12 mmol) of potassium hydroxide was added thereto. After heating to reflux for 50 hours, the solvent was distilled off, and ether was added thereto, followed by extraction with water. Hydrochloric acid was added to the aqueous layer, the precipitated crystals were filtered off and then washed with ether. The obtained crystals were recrystallized from dimethylformamide-water to obtain 445 mg (46% yield) of the desired compound.

Melting point: 236.5°–237.0° C.
Elemental analysis (%): C$_{26}$H$_{19}$F$_2$NO$_2$·0.6H$_2$O;
Calcd.: C 73.26, H 4.78, N 3.29 ;
Found: C 73.39, H 4.62, N 3.28.
IR (KBr) cm$^{-1}$: 2960, 1720, 1620, 1566, 1483, ;
NMR (DMSO-d6), δ (ppm): 8.52(1H, d, J=8Hz), 8.17–8.12 (1H, m), 7.70–7.32 (8H, m), 3.19–2.95 (3H, m), 1.44–1.31 (2H, m), 0.88 (3H, t, J=7Hz). MS (m/e): 415 (M+), 386

EXAMPLE 7

5,6-Dihydro-5,5-dimethyl-9-fluoro-3-(2fluorophenyl)-benz[acridine-7-carboxylic acid (Compound 7)

In 15 ml of ethanol were dissolved 2.25 g (8.39 mmol) of Compound u obtained in Reference Example 21 and 2.25 g (8.39 mmol) of 5-fluoroisatin, and 5 ml of water containing 2.14 g (41.9 mmol) of potassium hydroxide was added thereto. After heating to reflux for 20 hours, the solvent was distilled off, and ether was added thereto, followed by extraction with water. Hydrochloric acid was added to the aqueous layer, the precipitated crystals were filtered off and then washed with ether. The obtained crystals were recrystallized from ethanol to obtain 0.78 g (22% yield) of the desired compound.

Melting point: 269.2°–272.4° C.

Elemental analysis (%): C26H19F2NO20.3H20
Calcd.: C 74.02, H 4.69, N 3.33 ;
Found : C 74.20, H 4.40, N 3.59. ;
IR (KBr)cm$^{-1}$: 1599, 1503, 1408, 1246. ;
NMR (DMSO-d6), δ(ppm): 8.58(1H, d, J=8Hz),
8.22-8.16(1H, m), 7.75-7.32 (8H, m),
3.06(2H, s), 1.32(6H, s).
MS (m/e): 415 (M+), 400.

EXAMPLE 8

5,6-Dihydro-9-fluoro-3-(2-fluorophenyl)-6methylbenz-[acridine-7-carboxylic acid (Compound 8)

In 10 ml of ethanol were dissolved 1.50 g (5.90 mmol) of Compound x obtained in Reference Example 24 and 0.97 g (5.90 mmol) of 5-fluoroisatin, and 3 ml of water containing 1.65 g (29.5 mmol) of potassium hydroxide was added thereto. After heating to reflux for 60 hours, the solvent was distilled off, and ether was added thereto, followed by extraction with water. Hydrochloric acid was added to the aqueous layer and the precipitated crystals were filtered off. The obtained residue was separated and purified by silica gel column chromatography [elution solvent: chloroform-methanol-acetic acid (100:1:0.1)], and then recrystallized from ethanol to obtain 0.32 g (14% yield) of the desired compound.

Melting point: 257.4°-260.3° C.
Elemental analysis (%): C$_{25}$H$_{17}$F$_2$NO$_2$·0.2H$_2$O;
Calcd.: C 74.14, H 4.33, N 3.46 ;
Found : C 74.18, H 4.62, N 3.29. IR (KBr) cm$^{-1}$: 2360, 1703, 1560, 1506, 1485, 1239. NMR (CDC13), δ(ppm): 8.58(1H, d, J=8Hz),
8.24-8.18(1H, m), 7.64-7.15(8H, m),
3.58(1H, brs) , 3.31-3.23 (1H, m) ,
2.84-2.78(1H, m), 1.20(3H, d, J=7Hz).
MS (m/e): 401 (M+), 386.

EXAMPLE 9

6, 7-Dihydro-10-fluoro-3- (2-fluorophenyl)-5-methyl-5Hbenzo[6,7]cyclohepta[1,2-b]quinoline-8-carboxylic acid (Compound 9 )

In 3 ml of water containing 1.0 g (15.3 mmol) of potassium hydroxide was dissolved 0.51 g (3.06 mmol) of 5fluoroisatin, and 0.82 g (3.06 mmol) of Compound z obtained in Reference Example 26 and dissolved in 6 ml of ethanoldioxane (5: 1) was added thereto. After heating to reflux for 5 days, the solvent was distilled off, water-ether was added to the residue thereof for extraction, and the aqueous layer was washed with ether. The aqueous layer was filtered through celite. Acetic acid was added to the filtrate, and the precipitated crystals were filtered off. The obtained crystals were dried and then recrystallized from dimethylformamide-water to obtain 0.42 g (32% yield) of the desired compound.

Melting point: >300° C.
Elemental analysis (%): C$_{26}$H$_{19}$F$_2$NO$_2$·0.2H$_2$O;
Calcd.: C 74.52, H 4.67, N 3.34
Found: C 74.59, H 4.57, N 3.25. IR (KBr) cm$^{-1}$: 1712, 1628, 1502, 1243, 1216.
NMR (DMSO-d6), δ(ppm): 8.24-8.18(1H, m),
7.85-7.33(10H, m), 2.89-2.81(1H, m),
2.70-2.64(1H, m), 2.49-2.26(2H, m),
1.89-1.92(1H, m), 1.32(3H, d, J=7Hz).
MS (m/e): 415 (M+).

EXAMPLE 10

6,7-Dihydro-10-fluoro-3- (2-fluorophenyl)-6-methyl-5Hbenzo[6, 7 ]cyclohepta [1,2-hi quinoline-8-carboxylic acid ( Compound 10 )

In the same manner as in Example 9 except for using 0.45 g (2.69 mmol) of 5-fluoroisatin, 0.9 g (13.5 mmol) of potassium hydroxide and 0.72 g of Compound cc obtained in Reference Example 29, 0.38 g (34% yield) of the desired compound was obtained.

Melting point: >300° C .
Elemental analysis (%): C$_{26}$H$_{19}$F$_2$NO$_2$·0.2H$_2$O;
Calcd.: C 74.52, H 4.67, N 3.34
Found: C 74.53, H 4.57, N 3:35.
IR (KBr) cm$^{1-}$: 1703, 1610, 1494, 1236.
NMR ( DMSO-d6 ,δ(ppm):8.24-8.19(1H, m), 20 7.88 (1H, d, J=8Hz) , 7.79-7.33 (8H, m) ,
2.82-2.49(4H, m), 2.35-2.28(1H, m),
1.06 (3H, d, J=7Hz).
MS (m/e): 415 (M+).

EXAMPLE 11

6, 7-Dihydro-6, 6-dimethyl-10-fluoro-3-(2-fluorophenyl) -5Hbenzo [6, 7 ]cyclohepta [1,2 -hi quinoline-8-carboxylic acid ( Compound 11 )

In the same manner as in Example 9 except for using 0.46 g (2.76 mmol) of 5-fluoroisatin, 0.91 g (13.8 retool) of potassium hydroxide and 0.78 g of Compound ff obtained in Reference Example 32, 0.56 g (47% yield) of the desired compound was obtained.

Melting point: >300° C.
Elemental analysis (%): C$_{27}$H$_{21}$F$_2$NO$_2$·0.2H$_2$O
Calcd.: C 74.88, H 4.98, N 3.23 ;
Found: C 74.90, H 4.94, N 3.38.
IR (KBr) cm$^{-1}$: 1684, 1648, 1508.
NMR (DMSO-d6), δ(ppm): 8.25-8.19(1H, m),
7.88 (1H, d, J=8Hz), 7.80-7.33 (8H, m),
2.50 (2H, s), 2.37 (2H, s), 1.09 ( 6H, s).
MS (m/e): 429 (M+).

REFERENCE EXAMPLE 1

6-(2-Fluorophenyl)-l-indanone (Compound a)

To 10.7 g (80 mmol) of aluminum trichloride suspended in 100 ml of dichloroethane was added 5.46 g (42.7 mmol) of ethylmalonyl chloride. To the mixture was added 7.0 g (40 mmol) of 2-fluorobiphenyl, and the mixture was stirred at room temperature for 4 hours. The reaction solution was poured into hydrochloric acid containing ice, and extracted with chloroform. The organic layer was washed with hydrochloric acid and then dried over anhydrous magnesium sulfate. The solvent was distilled off under reduced pressure, and the residue was separated and purified by silica gel column chromatography [elution solvent: hexaneethyl acetate (30:1)], to obtain a mixture (70% yield) of ethyl 4-(2-fluorophenyl) benzoylacetate and ethyl 2-(2fluorophenyl)benzoylacetate.

To 7.9 g of the above mentioned mixture dissolved in 30 ml of trifluoroacetic acid was added 10.6 ml (66 mmol) of triethylsilane, and the mixture was stirred at 70° C for 2 hours. After the solvent was distilled off, chloroform and water were added to the residue for extraction. The organic layer was washed with an aqueous solution of sodium bicarbonate, and then dried over anhydrous magnesium sulfate. The solvent was distilled off under reduced pressure, and the residue was separated and purified by silica gel column chromatography [elution solvent: hexane-ethyl acetate (30:1)], to obtain 6.1 g (81% yield) of a mixture of ethyl 4-(2-fluorophenyl)benzylacetate and ethyl 2- (2-fluorophenyl) benzylacetate.

To 5.9 g of the above mentioned mixture dissolved in 20 ml of dioxane was added 20 ml of an aqueous solution of 4 N sodium hydroxide, and the mixture was heated to reflux for 2 hours. The solvent was distilled off under reduced pressure, and 50 ml of water was added thereto. The mixture was washed with ether, 20 ml of 6 N hydrochloric acid was added to the aqueous layer for acidification, followed by extraction with ethyl acetate. The organic layer was washed with saturated saline and then dried over anhydrous magnesium sulfate. The solvent was distilled off under reduced pressure to obtain 5.2 g (97% yield) of a mixture of 4-(2-fluorophenyl)benzylacetic acid and 2-(2fluorophenyl)benzylacetic acid.

To 5.1 g of the above mentioned mixture was added 50 ml of polyphosphoric acid, and the mixture was stirred at 80° C for 2 hours. The reaction product was poured into ice water and extracted with chloroform. The organic layer was washed with water and dried over anhydrous magnesium sulfate. The solvent was distilled off under reduced pressure, and the residue was separated and purified by silica gel column chromatography [elution solvent: hexane-ethyl acetate (30:1)], to obtain 2.9 g (54% yield) of the desired compound.

NMR (CDC13), δ(ppm): 7.93(1H, s),
7.81(1H, d, J=8Hz), 7.53-7.13(5H, m),
3.20(2H, t, J=6Hz), 2.75(2H, t, J=6Hz).
MS (m/e): 226 (M+).

REFERENCE EXAMPLE 2

5-(2-Fluorophenyl)indan (Compound b)

In 20 ml of trifluoroacetic acid was dissolved 1.6 g (7.1 mmol) of Compound a obtained in Reference Example 1 and 2.61 ml (16.3 mmol) of triethylsilane was added thereto. The mixture was stirred at 80° C. for 3 hours. The solvent was distilled off, and then chloroform and water were added to the residue for extraction. The organic layer was washed with an aqueous solution of sodium bicarbonate and then dried over anhydrous magnesium sulfate. The solvent was distilled off under reduced pressure and the residue was separated and purified by silica gel column chromatography [elution solvent: hexane]to obtain 1.38 g (92% yield) of the desired compound.

NMR (CDC13), δ(ppm): 7.44–7.10(7H, m),
2.99-2.92 (4H, m), 2.16-2.05 (2H, q, J=7Hz).
MS (m/e): 212 (M+).

REFERENCE EXAMPLE 3

5- (2-Fluorophenyl) -1-indanone (Compound c)

In 1 ml of propionic acid and 4 ml of acetic acid was dissolved 1.35 g of Compound b obtained in Reference Example 2, and 1.91 g (19.1 mmol) of chromic acid dissolved in 7.2 ml of acetic acid-water (7:1) was added thereto at 0° C. The mixture was stirred at room temperature for 2 hours. An aqueous solution of sodium sulfite and ethyl acetate were added to the reaction solution for extraction. The organic layer was washed with saline and then dried over anhydrous magnesium sulfate. The solvent was distilled off under reduced pressure and the residue was separated and purified by silica gel column chromatography [elution solvent: 4% ethyl acetate-hexane]to obtain 1.0 g (70% yield) of the desired compound.

NMR (CDC13), δ(ppm): 7.83(1H, d, J=8Hz),
7.66(1H, s), 7.56–7.18(5H, m), 3.21(2H, t, J=6Hz),
2.75 (2H, t, J=6HZ).
MS (m/e): 226 (M+).

REFERENCE EXAMPLE 4

3- [4- (2-Fluorophenyl)benzoyl]propanoic acid (Compound d)

To 6.2 g (46.5 mmol) of aluminum trichloride suspended in 50 ml of dichloroethane were added 3.02 g (30.2 retool) of succinic anhydride and 4.0 g (23.2 mmol) of 2-fluorobiphenyl were added thereto and the mixture was stirred at room temperature for 4 hours. The reaction solution was poured into hydrochloric acid containing ice, and extracted with chloroform. The organic layer was washed with water and then dried over anhydrous magnesium sulfate. The solvent was distilled off under reduced pressure and then recrystallized from chloroform to obtain 5.6 g (89% yield) of the desired compound.

NMR (CDC13), δ(ppm): 8.15(2H, d, J=7Hz),
7.73-7.00(7H, m), 3.35(2H, t, J=7Hz),
2.85 (2H, t, J=7Hz).
MS (m/e): 272 (M+), 255, 228.

REFERENCE EXAMPLE 5

4- [4- (2-Fluorophenyl)phenyl]butanoic acid (Compound e)

In 25 ml of trifluoroacetic acid was dissolved 5.21 g (19.1 mmol) of Compound d obtained in Reference Example 4, and 7.5 ml (46.5 mmol) of triethylsilane was added thereto. The mixture was stirred at 70° C. for 6 hours. The solvent was distilled off, and then chloroform and water were added to the residue for extraction. The organic layer was washed with water and then dried over anhydrous magnesium sulfate. The solvent was distilled off under reduced pressure and the residue was separated and purified by silica gel column chromatography [elution solvent: ethyl acetate-hexane (4: 1) ]to obtain 4.72 g (97% yield) of the desired compound.

NMR (CDCl3), δ(ppm): 7.65–6.93(8H, m),
2.80(2H, t, J=6Hz), 2.31(2H, t, J=eHz),
2.21-1.81 (2H, m).
MS (m/e): 258 (M+).

REFERENCE EXAMPLE 6

3,4-Dihydro-7- (2-fluorophenyl) -1- (2H)-naphthalenone (Compound f)

To 4.72 g (18.4 mmol) of Compound e obtained in Reference Example 5 was added 50 ml of polyphosphoric acid, and the mixture was stirred at 70° C for 4 hours. The reaction product was poured into ice water and extracted with chloroform. The organic layer was washed with water and dried over anhydrous magnesium sulfate. The solvent was distilled off under reduced pressure to obtain 4.11 g (94% yield) of the desired compound.

NMR (CDC13), δ(ppm): 8.15(1H, s), 7.71-6.90(6H, m),
2.93 (2H, t, J=5Hz), 2.60 (2H, t, J=5Hz),
2.30-1.92 (2H, m)o
MS (m/e): 240 (M+)

REFERENCE EXAMPLE 7

6- (2-Fluorophenyl) -1,2,3,4-tetrahydronaphthalene (Compound g)

In 40 ml of trifluoroacetic acid was dissolved 9.45 g (39.6 mmol) of Compound f obtained in Reference Example 6, and 15.3 ml (95.2 mmol) of triethylsilane was added thereto. The mixture was stirred at 70° C for 1 hour. The solvent was distilled off, and then chloroform and water were added to the residue for extraction. The organic layer was washed with water and then dried over anhydrous magnesium sulfate. The solvent was distilled off under reduced pressure to obtain the desired compound, which was used in the next reaction with no further purification.

NMR (CDCl3), $\delta$(ppm): 7.48–6.87(7H, m),
2.90–2.60 (4H, m) , 1.90–1.55 (4H, m).
MS (m/e): 226 (M+).

REFERENCE EXAMPLE 8

3,4-Dihydro-6- (2-fluorophenyl) -1 (2H) -naphthalenone (Compound h)

In 6 ml of propionic acid and 23 ml of acetic acid was dissolved 4.5 g of Compound g obtained in Reference Example 7, and 5.93 g (59.3 mmol) of chromic acid dissolved in 24 ml of acetic acid-water (7:1) was added thereto at 0° C. The mixture was stirred at room temperature for 12 hours. An aqueous solution of sodium sulfite and ethyl acetate were added to the reaction solution for extraction. The organic layer was washed with saline and then dried over anhydrous magnesium sulfate. The solvent was distilled off under reduced pressure and the residue was separated and purified by silica gel column chromatography [elution solvent: hexane-ethyl acetate (9:1)]to obtain 2.75 g (58% yield from Compound f) of the desired compound.

NMR (CDCl3), $\delta$(ppm): 8.10(1H, d, J=8Hz),
7.60–6.95(6H, m), 3.01(2H, t, J=6Hz),
2.69(2H, t, J=6Hz), 2.31–2.00(2h, m).
MS (m/e:) 240 (M+)

REFERENCE EXAMPLE 9

3-[4-(2-Fluorophenyl)benzoyl]butanoic acid (Compound i)

To 6.03 g (45.2 mmol) of aluminum trichloride suspended in 50 ml of dichloroethane were added 2.58 q (22.6 mmol) of anhydrous glutaric acid and 3.0 g (17.4 mmol) of 2fluorobiphenyl, and the mixture was stirred at room temperature for 3 hours. The reaction solution was poured jnto hydrochloric acid containing ice, and extracted with chloroform. The organic layer was washed with water and then dried over anhydrous magnesium sulfate. The solvent was distilled off under reduced pressure and then recrystallized from ethyl acetate to obtain 1.53 g (31% yield) of the desired compound.

NMR (DMSO-d6), $\delta$(ppm): 8.05(1H, d, J=8Hz),
7.76–7.21 (7H, m), 3.10 (2H, t, J=6Hz),
2.33 (2H, t, J=6Hz) , 2.10–1.75 (2H, m).
MS (m/e): 286 (M+).

REFERENCE EXAMPLE 10

5 - [4 - ( 2-Fluorophenyl ) phenyl ]pentanoic acid ( Compound j )

In 20 ml of trifluoroacetic acid was dissolved 3.8 g (13.3 mmol) of Compound i obtained in Reference Example 9, and 5.22 ml (32.5 mmol) of triethylsilane was added thereto. The mixture was stirred at 70° C for 3 hours. The solvent was distilled off, and then chloroform and water were added to the residue for extraction. The organic layer was washed with water and then dried over anhydrous magnesium sulfate. The solvent was distilled off under reduced pressure and then recrystallized from methylene chlorilde-hexane to obtain 2.7 g (75% yield) of the desired compound.

NMR (CDCl3), $\delta$(ppm): 7.56–6.99(8H, m),
2.83–2.57 (2H, m), 2.52–2.23 (2H, m),
1.93–1.50 (4H, m).
MS (m/e): 272 (M+), 254.

REFERENCE EXAMPLE 11

8- (2-Fluorophenyl) -1-benzosuberone (Compound k)

To 2.70 g (9.9 mmol) of Compound j obtained in Reference Example 10 was added 50 ml of polyphosphoric acid, and the mixture was stirred at 110° C. for 4 hours. The reaction product was poured into ice water and extracted with chloroform. The organic layer was washed with water and dried over anhydrous magnesium sulfate. The solvent was distilled off under reduced pressure to obtain 2.41 g (96% yield) of the desired compound.

NMR (CDCl3) , $\delta$(ppm): 7.91 (1H, s) , 7.65 (1H, d, J=8Hz) ,
7.51–7.10(5H, m), 2.98(2H, t, J=7Hz),
2.78(2H, t, J=7Hz), 1.99–1.81(4H, m).
MS (m/e): 254 (M+).

REFERENCE EXAMPLE 12

7 - ( 2 -Fluropheny 1 ) - 1H - 2, 3, 4,5 - t et rahydroben zocycloheptene (Compound l)

In 20 ml of trifluoroacetic acid was dissolved 2.36 g (9.2 mmol) of Compound k obtained in Reference Example 11, and 3.4 ml (21 mmol) of triethylsilane was added thereto. The mixture was stirred at 70° C. for 3 hours. The solvent was distilled off, and then chloroform and water were added to the residue for extraction. The organic layer was washed with water and then dried over anhydrous magnesium sulfate. The solvent was distilled off under reduced pressure to obtain the subject compound, which was used in the next reaction with no further purification.

NMR (CDCl3), $\delta$(ppm): 7.66–6.80(7H, m),
3.19–2.48(4H, m), 2.15–1.24(6H, m).
MS (m/e): 240 (M+).

REFERENCE EXAMPLE 13

7- (2-Fluorophenyl) -1-benzosuberone (Compound m)

In a mixture of 3 ml of propionic acid and 12 ml of acetic acid was dissolved 2.0 g of Compound Z obtained in Reference Example 12, and 2.5 g (24.9 mmol) of chromic acid dissolved in 12 ml of acetic acid-water (7:1) was added thereto at 0° C and the mixture was stirred at room temperature for 8 hours. An aqueous solution of sodium sulfite and ethyl acetate were added to the reaction solution for extraction. The organic layer was washed with saline and then dried over anhydrous magnesium sulfate. The solvent was distilled off under reduced pressure and the residue was separated and purified by silica gel column chromatography [elution solvent: hexane-ethyl acetate (9:1)]to obtain 0.43 g (20% yield from Compound f) of the desired compound.

NMR (CDCl3), $\delta$(ppm): 7.79(1H, d, J=8Hz), 7.57–7.00(6H, m), 2.97(2H, t, J=7Hz),
2.75(2H, t, J=7Hz), 2.04–1.65 (4H, m).
MS (m/e): 254 (M+).

REFERENCE EXAMPLE 14

8-(2-Fluorophenyl)-1-benzocyclooctanone (Compound n)

In 10 ml of dimethylformamide were dissolved 2.0 g (7.9 mmol) of 8-bromo-1-benzocyclooctanone, 0.27 g (0.23 mmol) of tetrakis(triphenylphosphine) palladium and 2.0 g (8.6 mmol) of silver oxide, 4.6 g (11.9 mmol) of o-fluorophenyltributyl tin was added thereto, and the mixture was stirred under an argon atmosphere at 120° C for 2 hours. After cooling, an aqueous solution of ammonium fluoride was added to the reaction solution, and then stirred at room temperature for 12 hours. The reaction solution was filtered through celite, washed with ethyl acetate and water, and then extracted. The organic layer was washed with saline and dried over anhydrous magnesium sulfate. The solvent was distilled off under reduced pressure and then separated and purified by silica gel column chromatography [elution solvent: hexane-ethyl acetate (9:1)]to obtain 0.84 g (40%) of the desired compound.

NMR (CDC13), δ(ppm): 7.79(1H, d, J=SHz),
7.49–7.12(6H, m), 3.13(2H, t, j=5Hz),
2.98 (2H, t, J=SHz), 1.94–1.80 (4H, m),
1.62–1.51 (2H, m).
MS (m/e): 268 (M+).

REFERENCE EXAMPLE 15

7-( 2-Fluorophenyl )-1-methyl- 1,2,3, 4-tetrahydronaphthalene ( Compound o )

To 12 ml of dimethylsulfoxide was added 1.0 g (25.0 retool) of 60% sodium hydroxide, and the mixture was stirred at 60° C for 1 hour. After allowing the solution to room temperature, 9.08 g (25.4 mmol) of methyltriphenylphosphonium bromide and 12 ml of tetrahydrofuran were added thereto. The mixture was stirred at room temperature for 20 minutes, 3.00 g (12.5 mmol) of Compound f obtained in Reference Example 6 dissolved in 15 ml of tetrahydrofuran was further added thereto, and the mixture was stirred at room temperature for 3 hours. Ether and water were added to the reaction solution for extraction. The organic layer was washed with saline and dried over anhydrous magnesium sulfate. The solvent was distilled off under reduced pressure, the residue was dissolved in 30 ml of ethanol, 150 mg of palladium/carbon was added thereto, and the mixture was stirred under a hydrogen atmosphere at room temperature for 4 hours. The mixture was then filtered through celite and the solvent was distilled off. The residue was separated and purified by silica gel column chromatography [elution solvent: hexane]to obtain 1.80 g (60%) of the desired compound.

NMR (CDC13), δ(ppm): 7.45–7.09 (7H, m),
3.00–2.78 (3H, m), 1.98–1.53 (4H, m),
1.33 (3H, d, J=7Hz).
MS (m/e): 240 (M+), 225.

REFERENCE EXAMPLE 16

3,4-Dihydro- 6- (2-fluorophenyl) -4-methyl-1 (2H)-naphthaienone (Compound p)

In a mixture of 3 ml of propionic acid and 10 mt of acetic acid was dissolved 1.85 g (7.7 mmol) of Compound o obtained in Reference Example 15, and 2.5 g (25 mmol) of chromic acid dissolved in 12 ml of acetic acid-water (7:1) was added thereto at 0° C. The mixture was stirred at room temperature for 4 hours. An aqueous solution of sodium sulfite and ethyl acetate were added to the reaction solution for extraction. The organic layer was washed with saline and then dried over anhydrous magnesium sulfate. The solvent was distilled off under reduced pressure and then the residue was separated and purified by silica gel column chromatography [elution solvent: hexane-ethyl acetate (10:1)]to obtain 0.88 g (45% yield) of the desired compound.

NMR (CDC13), δ(ppm): 8.10(1H, d, J=8Hz),
7.51–7.13(6H, m), 3.19–1.88(5H, m),
1.43 (3H, d, J=7Hz).
MS (m/e): 254 (M+), 226.

REFERENCE EXAMPLE 17

1-Ethyl-7- (2-fluorophenyl) -1,2,3, 4-tetrahydronaphthalene ( Compound q)

To 45 ml of dimethylsulfoxide was added 1.33 g (33.3 mmol) of 60% sodium hydride, and the mixture was stirred at 60° C for 1 hour. After allowing the solution to room temperature, 12.5 g (33.8 mmol) of methyltriphenylphosphonium bromide and 45 ml of tetrahydrofuran were added thereto, the mixture was stirred at room temperature for 20 minutes, 4.00 g (16.6 mmol) of Compound f obtained in Reference Example 6 dissolved in 15 ml of tetrahydrofuran was further added thereto, and the mixture was stirred at room temperature for 5 hours. Ether and water were added to the reaction solution for extraction. The organic layer was washed with saline and dried over anhydrous magnesium sulfate. The solvent was distilled off under reduced pressure, the residue was dissolved in 80 ml of ethanol, 168 mg of platinum dioxide was added thereto, and the mixture was stirred under a hydrogen atmosphere at room temperature for 4 hours. The mixture was then filtered through celite and the solvent was distilled off. The residue was separated and purified by silica gel column chromatography [elution solvent: hexane]to obtain 3.26 g (77%) of the desired compound.

NMR (CDCl3), δ(ppm:7.45–7.98(7H, m),
2.80–2.72(3H, m), 1.91–1.53(6H, m),
0.99 (3H, t, J=7Hz).
MS (m/e): 254 (M+).

REFERENCE EXAMPLE 18

3,4-Dihydro-4-ethyl-6- (2-fluorophenyl) -1 (2H)-naphthalenone (Compound r)

In a mixture of 4 ml of propionic acid and 15 ml of acetic acid was dissolved 3.26 g (12.8 mmol) of Compound q obtained in Reference Example 17, 4.09 g (40.9 mmol) of chromic acid dissolved in 24 ml of acetic acid-water (7:1) was added thereto at 0° C, and the mixture was stirred at room temperature for 4 hours. An aqueous solution of sodium sulfite and ethyl acetate were added to the reaction solution for extraction. The organic layer was washed with saline and then dried over anhydrous magnesium sulfate. The solvent was distilled off under reduced pressure and then the residue was separated and purified by silica gel column chromatography [elution solvent: hexane-ethyl acetate (30:1)]to obtain 1.39 g (41% yield) of the desired compound.

NMR (CDC13), δ(ppm): 8.10(1H, d, J=SHz),
7.50–7.13(6H, m), 2.94–1.70(7H, m),
1.05 (3H, t, J=7Hz).
MS (m/e): 268 (M+).

REFERENCE EXAMPLE 18

5- [4- (2-Fluorophenyl) phenyl ]-2-methyl-2-pentanol (Compound s)

In 50 ml of tetrahydrofuran was dissolved 5.00 g (19.4 retool) of Compound e obtained in Reference Example 5, 40 ml (120 retool) of an ether solution with 3 M concentration of methyl magnesium bromide was added thereto at 0° C, and then the mixture was heated to reflux for 1 hour. An aqueous solution of ammonium chloride and ether were added to the reaction solution for extraction. The organic layer was washed with saline and dried over anhydrous magnesium sulfate. The solvent was distilled off under reduced pressure, and then the residue was separated and purified by silica gel column chromatography [elution solvent: ethyl acetate-hexane (8:1)]to obtain 3.67 g (70% yield) of the desired compound.

NMR (CDC13), δ(ppm): 7.49–7.09(7H, m), 2.66(2H, t, J=7Hz), 1.78–1.51(m, 4H), 1.21(s, 6H).
MS (m/e): 258 (M+), 199.

REFERENCE EXAMPLE 20

7- (2-Fluorophenyl) -1, 1-dimethyl-i, 2,3, 4tetrahydronaphthalene (Compound t)

In 40 ml of dichloroethane was dissolved 3.67 g (13.5 mmol) of Compound s obtained in Reference Example 19, 2.0 g (15.0 mmol) of aluminum trichloride was added thereto, and the mixture was stirred at room temperature for 30 minutes. The reaction solution was poured into ice water, and chloroform was added thereto for extraction. The organic layer was washed with saline and then dried over anhydrous magnesium sulfate. The solvent was distilled off under reduced pressure to obtain 2.41 g (96% yield) of the desired compound. The solvent was distilled off under reduced pressure, and then, chloroform and water were added to the residue for extraction. The organic layer was washed with water, and dried over anhydrous magnesium sulfate. The solvent was distilled off under reduced pressure and then the residue was separated and purified by silica gel column chromatography [elution solvent: hexane]to obtain 3.00 g (88% yield) of the desired compound.

NMR (CDCl₃), δ(ppm): 7.77–7.33(7H, m), 3.05(2H, t, J=6Hz), 2.10–1.92(4H, m), 1.58(6H, s).
MS (m/e): 254 (M+), 239.

REFERENCE EXAMPLE 21

3,4-Dihydro-4,4-dimethyl-6- (2-fluorophenyl) -1 (2H) naphthalenone (Compound u)

In 3.5 ml of propionic acid and 17 ml of acetic acid was dissolved 2.80 g (11.1 mmol) of Compound t obtained in Reference Example 20, 3.54 g (35.4 mmol) of chromic acid dissolved in 14 ml of acetic acid-water (7:1) was added thereto at 0° C., and the mixture was stirred at room temperature for 4 hours. An aqueous solution of sodium sulfite and ethyl acetate were added to the reaction solution for extraction. The organic layer was washed with saline and then dried over anhydrous magnesium sulfate. The solvent was distilled off under reduced pressure and then the residue was separated and purified by silica gel column chromatography [elution solvent: hexane-ethyl acetate (10:1)]to obtain 2.25 g (76% yield) of the desired compound.

NMR (CDC13), δ(ppm): 8.09(1H, d, J=8Hz), 7.61–7.14(6H, m), 2.76(t, J=6Hz), 2.06 (2H, t, J=6Hz) , 1.44 (6H, s).
MS (m/e): 268 (M+), 253, 225.

REFERENCE EXAMPLE 22

3,4-Dihydro-7- (2-fluorophenyl) -2-methyl-1 (2H) -naphthalenone (Compound v)

In 20 ml of toluene was dissolved 2.00 g (8.32 mmol) of Compound f obtained in Reference Example 6, 1.45 g (18.3 mmol) of potassium hydroxide, 0.22 g (0.83 mmol) of 18- crown-6 and 6.8 ml (110 mmol) of methyl iodide were thereto, and the mixture was stirred at room temperature for 4 hours. Ammonium chloride and ethyl acetate were added to the reaction solution for extraction. The organic layer was washed with saline and then dried over anhydrous magnesium sulfate. The solvent was distilled off under reduced pressure and then the residue was separated and purified by silica gel column chromatography [elution solvent: hexaneethyl acetate (50:1)]to obtain 0.89 g (42% yield) of the desired compound.

NMR (CDC13), δ(ppm): 8.20(1H, s), 7.69–7.11(6H, m),
3.09–1.84 (5H, m), 1.30 (3H, d, J=7Hz).
MS (m/e): 254 (M+) , 212 .

REFERENCE EXAMPLE 23

7- (2-Fluorophenyl) -2-methyl-I, 2,3, 4-tetrahydronaphthalene (Compound w)

In 15 ml of trifluoroacetic acid was dissolved 2.16 g (8.49 mmol) of Compound v obtained in Reference Example 22, 3.26 ml (20.4 mmol) of triethylsilane was added thereto, and the mixture was stirred at 70° C. for 30 minutes. The solvent was distilled off, and then chloroform and water were added to the residue for extraction. The organic layer was washed with water and then dried over anhydrous magnesium sulfate. The solvent was distilled off under reduced pressure to obtain the desired compound, which was used in the next reaction with no further purification.

NMR (CDC13), δ(ppm): 7.46–7.09(7H, m), 2.92–1.38 (7H, m), 1.08 (3H, d, J=7Hz).
MS (m/e): 240 (M+), 198.

REFERENCE EXAMPLE 24

3,4-Dihydro-6- (2-fluorophenyl) -3-methyl-1 (2H) -naphthalenone (Compound x)

In a mixture of 2.7 ml of propionic acid and 10 ml of acetic acid was dissolved 2.3 g of Compound w obtained in Reference Example 23, 2.71 g (2.71 mmol) of chromic acid dissolved in 10 ml of acetic acid-water (7:1) was added thereto at 0° C, and the mixture was stirred at room temperature for 3 hours. An aqueous solution of sodium sulfite and ethyl acetate were added to the reaction solution for extraction. The organic layer was washed with saline and then dried over anhydrous magnesium sulfate. The -solvent was distilled off under reduced pressure and then the residue was separated and purified by silica gel column chromatography [elution solvent: hexane-ethyl acetate (10:1)]to obtain 2.15 g (70% yield) of the desired compound.

NMR (CDC13), δ(ppm): 8.09(1H, d, J=8Hz), 7.50–7.13(6H, m), 3.05–2.32(5H, m),
1.17 (3H, d, J=7Hz).
(m/e): 254 (M+), 212.

REFERENCE EXAMPLE 25

8-(2-Fluorophenyl)-1-methyl-ill-2,3,4,5tetrahydrobenzocycloheptene (Compound y)

In 20 ml of tetrahydrofuran was dissolved 2.50 g (9.84 mmol) of Compound k obtained in Reference Example 11, 6.7 ml (19.68 mmol) of an ether solution with 3 M concentration of methyl magnesium bromide was added thereto, and then the mixture was heated to reflux for 10 hours. The reaction solution was allowed to room temperature, a saturated aqueous solution of ammonium chloride was added thereto to stop the reaction, and ether was added thereto for extraction. The organic layer was washed with water and with saturated saline and then dried over anhydrous magnesium sulfate. The solvent was distilled off under reduced pressure, and then the residue was separated and purified by silica gel column chromatography [elution solvent: hexane-ethyl acetate (25: 1)]. To 2.0 g of the obtained compound were added 2.85 ml (17.8 mmol) of triethylsilane and 10 ml of trifluoroacetic acid, and the mixture was stirred at 60° C. for 1 hour. The solvent was distilled off under reduced pressure, chloroform was added thereto for extraction and the organic layer was washed with water and dried over anhydrous magnesium sulfate. The solvent was distilled off under reduced pressure, and then separated and purified by silica gel column chromatography [elution solvent: hexane]to obtain the desired compound, which was used in the next reaction with no further purification.

NMR (CDC13), δ(ppm): 7.47–7.08 (7H, m),
3.09 (1H, q, J=VHz), 2.96–2.78 (2H, m),
1.98–1.69 (4}{, m), 1.54–1.30 (2H, m),
1.37 (3H, d, J=7Hz).
MS (m/e): 254 (M+).

REFERENCE EXAMPLE 26

7-(2-Fluorophenyl)-5-methyl-l-benzosuberone (Compound z)

In a mixture of 1 ml of propionic acid and 10 ml of acetic acid was dissolved 1.60 g (6.29 mmol) of Compound y obtained in Reference Example 25, and 1.90 g (18.9 retool) of chromic acid dissolved in 8 ml of acetic acid-water (7:1) was added thereto at 0° C. The mixture was stirred at room temperature for 6 hours, and an aqueous solution of sodium sulfite was added thereto to stop the reaction. The solvent was distilled off under reduced pressure, and then ethyl acetate and water were added to the residue for extraction. The organic layer was washed with water and with saturated saline, and then dried over anhydrous magnesium sulfate. The solvent was distilled off under reduced pressure and then the residue was separated and purified by silica gel column chromatography [elution solvent: hexane-ethyl acetate (25:1)]to obtain 0.35 g (21% yield) of the desired compound.

NMR (CDC13), δ(ppm): 7.64(1H, d, J=8Hz),
7.49–7.13<6H, m), 3.21–3.13{1H, m),
2.82–2.58 (2H, m), 2.08–1.83 (2H, m),
1.78–1.55(2H, m), 1.42(3H, d, J=7Hz).
MS (m/e): 268 (M+).

REFERENCE EXAMPLE 27

8-(2-Fluorophenyl)-2-methyl-!-benzosuberone (Compound aa)

In 70 ml of toluene was dissolved 2.50 g (9.84 mmol) of Compound k obtained in Reference Example 11, 1.32 ml (14.8 mmol) of pyrrolidine and 50 mg of tosylic acid were added thereto, and the mixture was heated to reflux for 6 hours under azeotropic dehydration. The solvent was distilled off, the residue was allowed to room temperature, 100 ml of dioxane and 1.04 ml (16.7 retool) of methyl iodide were added thereto, and the mixture was heated to reflux for 6 hours. The reaction solution was allowed to room temperature, 2 ml of water, and then 1 ml of acetic acid, were added thereto, and the mixture was stirred for 30 minutes. The solvent was distilled off under reduced pressure, and chloroform was added to the residue for extraction. The organic layer was washed with water and then dried over anhydrous magnesium sulfate. The solvent was distilled off under reduced pressure and then the residue was separated and purified by silica gel column chromatography [elution solvent: hexaneethyl acetate (30:1)]to obtain 1.66 g (63% yield) of the desired compound.

NMR (CDC13), δ(ppm): 7.85(1H, s)
7.48–7.10 (6H, m), 3.06–2.93 (3H, m),
2.12–1.61 (4H, m), 1.24 (3H, d, J=7Hz)o
MS (m/e): 268 (M+).

REFERENCE EXAMPLE 28

8-(2-Fluorophenyl)-2-methyl-ill-2,3,4,5tetrahydrobenzocycloheptene (Compound bb)

In 25 ml of trifluoroacetic acid was dissolved 2.98 g (11.1 mmol) of Compound aa obtained in Reference Example 27, 4.28 ml (26.6 mmol) of triethylsilane was added thereto, and the mixture was stirred at 70° C for 2 hours. The solvent was distilled off, chloroform and water were added to the residue for extraction, and the organic layer was washed with water and then dried over anhydrous magnesium sulfate. The solvent was distilled off under reduced pressure anG separated and purified by silica gel column chromatography [elution solvent: hexane]to obtain the desired compound, which was used in the next reaction with no further purification.

NMR (CDCl₃), δ(ppm): 7.43–7.10(7H, m),
2.81–2.71 (4H, m), 1.99–1.44 (5H, m),
0.97 (3H, d, J=8Hz).
MS (m/e): 254 (M+).

REFERENCE EXAMPLE 29

7-(2-Fluorophenyl)-4-methyl-1-benzosuberone (Compound cc)

In 15 ml of acetic acid was dissolved 2.76 g (10.9 mmol) of Compound bb obtained in Reference Example 28, and 3.27 g (32.7 mmol) of chromic acid dissolved in 8 ml of acetic acid-water (7:1) was added thereto at 0° C. The mixture was stirred at room temperature for 6 hours, and an aqueous solution of sodium sulfite was added thereto to stop the reaction. The solvent was distilled off under reduced pressure, and then ethyl acetate and water were added to the residue for extraction. The organic layer was washed with water and with saturated saline, and then dried over anhydrous magnesium sulfate. The solvent was distilled off under reduced pressure and then the residue was separated and purified by silica gel column chromatography [elution solvent: hexane-ethyl acetate (25: 1) to obtain 0.60 g (21% yield) of the desired compound.

NMR (CDC13), δ(ppm): 7.80(1H, d, J=SHz),
7.51–7.13(6H, m), 3.07–2.99(1H, m),
2.85–2.61(3H, m), 2.21–2.11 (1H, m),
2.02–1.90(1H, m), 1.47–1.35(1H, m), 1.04 (3H, d, J=7Hz).
MS (m/e): 268 (M+).

REFERENCE EXAMPLE 30

2,2-Dimethyl-8- (2-fluorophenyl) -1-benzosuberone (Compound dd)

In 30 ml of tetrahydrofuran was dissolved 2.50 g (9.84 retool) of Compound k obtained in Reference Example 11, 2.67 g (24.6 mmol) of potassium tert-butoxide was added thereto, and the mixture was stirred for 30 minutes. To the mixture was added 1.53 ml (24.6 mmol) of methyl iodide at 0° C., stirred at room temperature for 8 hours, and water was added thereto to stop the reaction. Ethyl acetate was added thereto for extraction, and the organic layer was washed with water and with saturated saline and then dried over anhydrous magnesium sulfate. The solvent was distilled off under reduced pressure, and then the residue was separated and purified by silica gel column chromatography [elution solvent: hexane-ethyl acetate (50:1)]to obtain 1.80 g (65% yield) of the desired compound.

NMR (CDC13), δ(ppm): 7.57–7.13 (7H, m),
2.81 (2H, t, J=7Hz), 1.98–1.91 (2H, m), 10 1.74–1.69(2H, m), 1.20(6H, s)0

REFERENCE EXAMPLE 31

2, 2-Dimethyl-8- (2-fluorophenyl) 1H-2,3,4,5-tetrahydrobenzocycloheptene (Compound ee)

In 25 ml of trifluoroacetic acid was dissolved 2.22 g (7.87 mol) of Compound dd obtained in Reference Example 30, 3.03 ml (18.9 mmol) of triethylsilane was added thereto, and the mixture was stirred at 70° C for 2 hours. The solvent was distilled off, chloroform and water were added to the residue for extraction, and the organic layer was washed with water and then dried over anhydrous magnesium sulfate. The solvent was distilled off under reduced pressure and separated and purified by silica gel column chromatography [elution solvent: hexane]to obtain the desired compound, which was used in the next reaction with no further purification.

NMR (CDCl₃), δ(ppm): 7.45–7.08(7H, m),
2.81–2.70(4H, m), 1.69–1.47(4H, m), 0.86(6H, s).
MS (m/e): 268 (M+).

REFERENCE EXAMPLE 32

4,4-Dimethyl-V- (2-fluorophenyl) -1-benzosuberone (Compound ff)

In 15 ml of acetic acid was dissolved 2.10 g (7.84 mmol) of Compound ee obtained in Reference Example 31, and 2.35 g (23.5 mmol) of chromic acid dissolved in 8 ml of acetic acid-water (7:1) was added thereto at 0° C. The mixture was stirred at room temperature for 6 hours, and an aqueous solution of sodium sulfite was added thereto to stop the reaction. The solvent was distilled off under reduced pressure, and then ethyl acetate and water were added to the residue for extraction. The organic layer was washed with water and with saturated saline, and then dried over anhydrous magnesium sulfate. The solvent was distilled off under reduced pressure and then the residue was separated and purified by silica gel column chromatography [elution solvent: hexane-ethyl acetate (25:1)]to obtain 0.79 g (36% yield) of the desired compound.

NMR (CDC13), δ(ppm): 7.81(1H, d, J=8Hz),
7.52–7.13 (6H, m), 2.71–2.63 (4H, m),
1.55–1.51(2H, m), 1.05(6H, s).
MS (m/e): 282 (M+).

PREPARATION EXAMPLE 1: TABLETS

Tablets each having the following composition were prepared in a conventional manner.

| Prescription | Compound 1 | 10 mg |
| --- | --- | --- |
| | Lactose | 30 mg |
| | Potato starch | 15 mg |
| | Polyvinyl alcohol | 1.5 mg |
| | Magnesium stearate | 0.5 mg |

PREPARATION EXAMPLE 2: CAPSULES

Capsules each having the following composition were prepared in a conventional manner.

| Prescription | Compound 1 | 10 mg |
| --- | --- | --- |
| | Lactose | 100 mg |
| | Magnesium stearate | 2.5 mg |

A mixture of the above ingredients was loaded into gelatin capsules.

PREPARATION EXAMPLE 3: INJECTION

Injections having the following composition were prepared in a conventional manner.

| Prescription | Compound 1 | 10 mg |
| --- | --- | --- |
| | Sodium chloride | 20 mg |

To the ingredients was added distilled water for injection to make the total volume 5 ml (per arepule).

INDUSTRIAL APPLICABILITY

According to the present invention, there can be provided novel tetracyclic compounds which are useful as immunosuppressive agents.

What is claimed is:

1. A novel tetracyclic compound represented by formula (I)

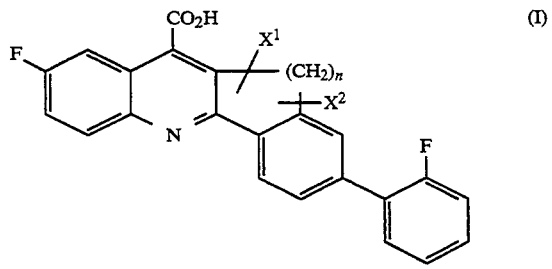

(wherein each of $X^1$ and $X^2$ independently represents hydrogen or lower alkyl; n represents an integer of 1 to 4, or a pharmaceutically acceptable salt thereof.

* * * * *

UNITED STATES PATENT AND TRADEMARK OFFICE
CERTIFICATE OF CORRECTION

PATENT NO. : 5,371,225

DATED : December 6, 1994

INVENTORS : FUMIO SUZUKI ET AL.    Page 1 of 10

It is certified that error appears in the above-identified patent and that said Letters Patent is hereby corrected as shown below:

COLUMN 1

Line 35, "carboxyl" should read --carboxylate (DUP785) is--.
Line 64, "t6" should read --to--.

COLUMN 2

Line 17, "The" should read --¶ The--.

COLUMN 3

Line 46, "Compound" should read --¶ Compound--.

COLUMN 4

Line 34, "#rom" should read --from--.
Line 41, "fim" should read --um--.

COLUMN 5

Line 22, "(II)" should read --(XII)--.
Line 61, "J.Org." should read --[J.Org.--.
Line 63, "Angew." should read --[Angew.--.

COLUMN 8

Line 30, "(I)" should read --(XVII)--.

UNITED STATES PATENT AND TRADEMARK OFFICE
CERTIFICATE OF CORRECTION

PATENT NO. : 5,371,225

DATED : December 6, 1994

INVENTORS : FUMIO SUZUKI ET AL.

It is certified that error appears in the above-identified patent and that said Letters Patent is hereby corrected as shown below:

COLUMN 9

Comp. (I-d), "$< \begin{array}{c} X^{1a} \\ X^{2a} \end{array}$" should read $-- < \begin{array}{c} X^2 \\ X^{1a} \end{array} --$.

Line 28, "$X^{1a}$ $X^2$" should read --$X^{1a}$, $X^2$--.
Line 48, "p-toluenesutfonic" should read --p-toluenesulfonic--.

COLUMN 10

Line 37, "pruification" should read --purification--.
Line 42, "pharmaceuticaly" should read --pharmaceutically--.

COLUMN 11

Line 45, "2mercaptoethanol" should read --2-mercaptoethanol--.

COLUMN 12

Line 48, "groups" should read --groups of--.

COLUMN 13

Line 3, "4[Japanese" should read --4-quinolinecarboxylate [Japanese--.

UNITED STATES PATENT AND TRADEMARK OFFICE
CERTIFICATE OF CORRECTION

PATENT NO. : 5,371,225

DATED : December 6, 1994

INVENTORS : FUMIO SUZUKI ET AL.

It is certified that error appears in the above-identified patent and that said Letters Patent is hereby corrected as shown below:

COLUMN 14

Line 9, "compound swelling rates a test" should be deleted.
Line 10, "(dose: administered group" should be deleted.
Line 11, "the 1 mg/kg)," should read --the swelling rates of a test compound-administered group (dose: 1 mg/kg),--.
Line 34, "6carboxylic" should read --6-carboxylic--.
Line 35, "(10 tool)" should read --(10mmol)--.
Line 36, "(2 tool)" should read --(2mmol)--.
Line 37, "5fluoroisatin," should read --5-fluorosatin,-- and "(2 retool)" should read --(2mmol)--.
Line 48, "$C_{23}H_{13}F_2NO_2 \cdot 0.5H_2O$;" should read --$C_{23}H_{13}F_2NO_2 \cdot 0.5H_2O$;--.
Line 58, "ben z" should read --benz--.
Line 59, "7carboxylic" should read --7-carboxylic--.

COLUMN 15

Line 6, "C24H15F2NO2 - 0.2HO;" should read --$C_{24}H_{15}F_2NO_2 \cdot 0.2H_2O$;--.
Line 7, "C73 . 73, H 3 . 97, N3 . 58;" should read --C 73.73, H 3.97, N 3.58;--.
Line 8, "N3 . 67." should read --N 3.67.--.
Line 10, "J=SHz)," should read --J=8Hz),--.
Line 16, "-5Hbenzo" should read -- -5H-benzo--.

UNITED STATES PATENT AND TRADEMARK OFFICE
CERTIFICATE OF CORRECTION

PATENT NO. : 5,371,225

DATED : December 6, 1994

INVENTORS : FUMIO SUZUKI ET AL.

It is certified that error appears in the above-identified patent and that said Letters Patent is hereby corrected as shown below:

COLUMN 15 (cont'd.)

Line 32, "$C_{25}H_{17}F_2NO_2 \cdot 0.4H_2O;$" should read
--$C_{25}H_{17}F_2NO_2 \cdot 0.4H_2O;$--.
Line 43, "-5,6,7,8tetrahydroben-" should read
--5,6,7,8-tetrahydroben- --.
Line 56, "column"" should read --column--.

COLUMN 16

Line 3, "-5methylbenz[-" should read -- -5-methylbenz[- --.
Line 27, "10" should be deleted.
Line 28, "(2fluorophenyl)benz" should read
--(2-fluorophenyl)benz--.
Line 47, "1483,;" should read --1483.--.
Line 48, "8 (ppm):" should read --$\delta$(ppm):--.
Line 54, "3-(2fluorophenyl)-" should read
--3-(2-fluorophenyl)- --.
Line 55, "benz[acridine-" should read --benz[c]acridine- --.

COLUMN 17

Line 1, "C26H19F2NO20.3H20" should read --$C_{26}H_{19}F_2NO_2 \cdot 0.3H_2O$--.
Line 11, "6methylbenz-" should read --6-methylbenz- --.
Line 12, "[acridine-" should read --[c]acridine- --.
Line 32, "(CDC13)," should read --(CDCl$_3$),--.
Line 42, "5Hbenzo" should read --5H-benzo--.
Line 46, "5fluoroisatin," should read --5-fluoroisatin,--.

UNITED STATES PATENT AND TRADEMARK OFFICE
CERTIFICATE OF CORRECTION

PATENT NO. : 5,371,225

DATED : December 6, 1994

INVENTORS : FUMIO SUZUKI ET AL.

It is certified that error appears in the above-identified patent and that said Letters Patent is hereby corrected as shown below:

COLUMN 18

Line 4, "5Hbenzo" should read --5H-benzo-- and --"[1,2-hi" should read --[1,2-b]--.
Line 14, "N 3:35." should read --N 3.35.--.
Line 15, "$cm^{1-}$:" should read --$cm^{-1}$:--.
Line 16, "(DMSO-d6," should read --(DMSO-d6),-- and "20" should be deleted.
Line 24, "-5Hbenzo" should read -- -5H-benzo-- and "[1,2 -hi" should read --[1,2-b]--.
Line 28, "(13.8 retool)" should read --(13.8 mmol)--.
Line 57, "2-(2fluoro-" should read --2-(2-fluoro- --.

COLUMN 19

Line 8, "cf" should read --of--.
Line 18, "2-(2fluorophenyl)benzyla-" should read --2-(2-fluorophenyl)benzyla- --.
Line 30, "(CDCl3)," should read --($CDCl_3$),--.
Line 50, "(CDCl3)," should read --($CDCl_3$),--.
Line 62, "f6r" should read --for--.

COLUMN 20

Line 3, "(CDCl3)," should read --($CDCl_3$),--.
Line 5, "J=6HZ)." should read --J=6Hz.--.
Line 13, "(30.2 retool)" should read --(30.2 mmol)--.
Line 24, "(CDCl3)," should read --($CDCl_3$),--.
Line 47, "J=eHz)," should read --J=6Hz),--.

UNITED STATES PATENT AND TRADEMARK OFFICE
CERTIFICATE OF CORRECTION

PATENT NO. : 5,371,225

DATED : December 6, 1994

INVENTORS : FUMIO SUZUKI ET AL.

It is certified that error appears in the above-identified patent and that said Letters Patent is hereby corrected as shown below:

COLUMN 20 (cont'd.)

Line 64, "(CDC13)," should read --$(CDCl_3)$,--.
Line 67, "(2H,m)o" should read --(2H,m)--.

COLUMN 21

Line 16, "(CDC13)," should read --$(CDCl_3)$,--.
Line 37, "(CDC13)," should read --$(CDCl_3)$,--.
Line 39, "2.31-2.00(2h,m)." should read
    --2.31-2.00(2H,m).--.
Line 46, "2.58 q" should read --2.58 g--.
Line 48, "2fluorobiphenyl," should read
    --2-fluorobiphenyl,--.
Line 50, "jnto" should read --into--.

COLUMN 22

Line 7, "chlorilde-hexane" should read --chloride-hexane--.
Line 25, "(CDC13)," should read --$(CDCl_3)$,--.
Line 33, "( 2 -Fluropheny l )" should read
    --(2-Fluorophenyl)-- and "t et rahydroben"
    should read --tetrahydro-ben- --.
Line 46, "(CDC13)," should read --$(CDCl_3)$,--.
Line 68, "(CDC13)," should read --$(CDCl_3)$,--.

COLUMN 23

Line 25, "(CDC13)," should read --$(CDCl_3)$,-- and
    "J=SHz)," should read --J=8Hz),--.

UNITED STATES PATENT AND TRADEMARK OFFICE
CERTIFICATE OF CORRECTION

PATENT NO. : 5,371,225

DATED : December 6, 1994

INVENTORS : FUMIO SUZUKI ET AL.

It is certified that error appears in the above-identified patent and that said Letters Patent is hereby corrected as shown below:

COLUMN 23 (cont'd.)

Line 26, "j=5Hz)," should read --J=5Hz),--.
Line 27, "J=SHz)," should read --J=5Hz),--.
Line 35, "retool)" should read --mmol)--.
Line 56, "(CDCl3)," should read --(CDl$_3$),--.
Line 63, "-naphtaienone" should read -- -naphthalenone--.
Line 65, "10 mt" should read --10 ml--.

COLUMN 24

Line 11, "(CDCl3)," should read --(CDCl$_3$),--.
Line 30, "the"" should read --the--.
Line 42, "δ(ppm:7.45-7.98(7H,m)," should read
    --δ(ppm):7.45-7.08(7H,m),--.
Line 65, "(CDCl3)," should read --(CDCl$_3$),-- and
    "J=SHz)," should read --J=8Hz),--.

COLUMN 25

Line 6, "retool)" should read --mmol)--.
Line 7, "(120 retool)" should read --(120mmol)--.
Line 19, "(CDCl3)," should read --(CDCl$_3$),--.
Line 24, "1,dimethyl-i,2,3," should read
    --1,dimethyl-1,2,3,--.
Line 25, "4tetrahydronaphthalene" should read
    --4-tetrahydronaphthalene--.
Line 68, "(CDCl3)," should read --(CDCl$_3$),--.

UNITED STATES PATENT AND TRADEMARK OFFICE
CERTIFICATE OF CORRECTION

PATENT NO. : 5,371,225

DATED : December 6, 1994

INVENTORS : FUMIO SUZUKI ET AL.

It is certified that error appears in the above-identified patent and that said Letters Patent is hereby corrected as shown below:

COLUMN 26

Line 12, "were" should read --were added--.
Line 23, "(CDC13)," should read --(CDCl$_3$),--.
Line 29, "-2-methyl-I, 2,3," should read
-- -2-methyl-1,2,3,--.
Line 43, "(CDC13)," should read --(CDCl$_3$),--.
Line 59, "-solvent" should read --solvent--.
Line 65, "(CDC13)," should read --(CDCl$_3$),--.

COLUMN 27

Line 3, "-1-methyl-ill-2,3," should read
-- -1-methyl-1H-2,3,--.
Line 4, "4,5tetrahydrobenzocycloheptene" should read
--4,5-tetrahydrobenzocycloheptene--.
Line 31, "(CDC13)," should read --(CDCl$_3$),--.
Line 32, "J=VHz)," should read --J=7Hz),--.
Line 33, "(4}{,m)," should read --(4H,m),--.
Line 43, "(18.9 retool)" should read --(18.9 mmol)--.
Line 57, "(CDC13)," should read --(CDCl$_3$),--.
Line 58, "<6H,m)," should read --(6H,m),-- and
"{1H,m)," should read --(1H,m),--
Line 64, "-2-methyl-!-" should read -- -2-methyl-1- --.

COLUMN 28

Line 6, "retool)" should read --mmol)--.
Line 19, "(CDC13)," should read --(CDCl$_3$),--.
Line 21, "J=7Hz)o" should read --J=7Hz)--.

UNITED STATES PATENT AND TRADEMARK OFFICE
CERTIFICATE OF CORRECTION

PATENT NO. : 5,371,225

DATED : December 6, 1994

INVENTORS : FUMIO SUZUKI ET AL.

It is certified that error appears in the above-identified patent and that said Letters Patent is hereby corrected as shown below:

COLUMN 28 (cont'd.)

Line 25, "-2-methyl-ill-2,3," should read
    -- -2-methyl-1H-2,3,--.
Line 26, "4,5tetrahydrobenzocycloheptene" should read
    --4,5-tetrahydrobenzocycloheptene--.
Line 35, "anG" should read --and--.
Line 65, "(CDC13)," should read --(CDCl$_3$),-- and
    "J=SHz)," should read --J=8Hz),--.

COLUMN 29

Line 8, "retool)" should read --mmol)--.
Line 22, "(CDC13)," should read --(CDCl$_3$),--.
Line 23, "10" should be deleted.
Line 24, "1.20(6H, s)0" should read --1.20(6H, s) ¶ MS
    (m/e): 282 (M$^+$)--.
Line 27, "1H-2,3,4,5-" should read -- -1H-2,3,4,5- --.
Line 31, "(7.87 mol)" should read --(7.87 mmol)--.
Line 48, "4,4-Dimethyl-V-" should read --4,4-Dimethyl-7- --.

UNITED STATES PATENT AND TRADEMARK OFFICE
CERTIFICATE OF CORRECTION

PATENT NO. : 5,371,225

DATED : December 6, 1994

INVENTORS : FUMIO SUZUKI ET AL.

It is certified that error appears in the above-identified patent and that said Letters Patent is hereby corrected as shown below:

COLUMN 30

Line 3, "(CDC13)," should read --(CDCl$_3$),--.
Line 30, "INJECTION" should read --INJECTIONS--.
Line 39, "arepule)." should read --ampule).--.
Line 61, "(" should be deleted.

Signed and Sealed this

Sixth Day of June, 1995

BRUCE LEHMAN

*Attesting Officer*    Commissioner of Patents and Trademarks